US010786275B2

(12) United States Patent
Downey

(10) Patent No.: US 10,786,275 B2
(45) Date of Patent: *Sep. 29, 2020

(54) ULTRASONIC SURGICAL TOOL SYSTEM INCLUDING A TIP CAPABLE OF SIMULTANEOUS LONGITUDINAL AND TORSIONAL MOVEMENT AND A CONSOLE CAPABLE OF APPLYING A DRIVE SIGNAL TO THE TIP SO THE TIP ENGAGES IN SUBSTANTIALLY TORSIONAL OSCILLATIONS

(71) Applicant: Stryker Corporation, Kalamazoo, MI (US)

(72) Inventor: Adam Downey, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 158 days.

This patent is subject to a terminal disclaimer.

(21) Appl. No.: 16/062,969

(22) PCT Filed: Dec. 14, 2016

(86) PCT No.: PCT/US2016/066635
§ 371 (c)(1),
(2) Date: Jun. 15, 2018

(87) PCT Pub. No.: WO2017/106329
PCT Pub. Date: Jun. 22, 2017

(65) Prior Publication Data
US 2018/0368877 A1 Dec. 27, 2018

Related U.S. Application Data
(60) Provisional application No. 62/269,542, filed on Dec. 18, 2015.

(51) Int. Cl.
A61B 17/32 (2006.01)
A61B 17/00 (2006.01)

(52) U.S. Cl.
CPC .......... *A61B 17/320068* (2013.01); *A61B 2017/00017* (2013.01); *A61B 2017/00132* (2013.01);
(Continued)

(58) Field of Classification Search
CPC .......... A61F 17/32; A61F 17/320092; A61F 17/320068; A61F 2017/00146;
(Continued)

(56) References Cited

U.S. PATENT DOCUMENTS 3,990,452 A * 11/1976 Murry .............. A61B 17/22012
606/169
4,705,980 A 11/1987 Mishiro
(Continued)

FOREIGN PATENT DOCUMENTS

EP 2362752 A1 9/2011
WO 2005084553 A1 9/2005
(Continued)

OTHER PUBLICATIONS

International Search Report for Application No. PCT/US2016/066635 dated Mar. 21, 2017, 3 pages.

*Primary Examiner* — Vi X Nguyen
(74) *Attorney, Agent, or Firm* — Howard & Howard Attorneys PLLC

(57) ABSTRACT

An ultrasonic tool system with a console (230) and a tip (142) that has a distal end that when vibrated vibrates both longitudinally and torsionally. The console applies a drive signal to the drivers (36) that vibrate the tip that is at a longitudinal mechanical cancelation frequency. Consequently, when the tip is vibrated, at the distal end the
(Continued)

longitudinal component of a first resonant mode of the tip cancel out the longitudinal component of the second resonant move of the tip so the distal end of the tip engages in vibrations that substantially torsional and only minimally longitudinal.

20 Claims, 13 Drawing Sheets

(52) U.S. Cl.
CPC ............... *A61B 2017/00146* (2013.01); *A61B 2017/320098* (2017.08)

(58) Field of Classification Search
CPC ........ A61F 2017/320098; A61F 2017/320072; A61F 9/00745
See application file for complete search history.

(56) References Cited

U.S. PATENT DOCUMENTS

| | | |
|---|---|---|
| 6,955,680 B2 | 10/2005 | Satou et al. |
| 10,561,435 B2* | 2/2020 | Downey .......... A61B 17/32006 |
| 2003/0045887 A1 | 3/2003 | Sakurai et al. |
| 2003/0125620 A1 | 7/2003 | Satou et al. |
| 2009/0131885 A1* | 5/2009 | Akahoshi ............... A61M 1/008 |
| | | 604/272 |
| 2012/0293044 A1 | 11/2012 | Bromfield |

FOREIGN PATENT DOCUMENTS

| | | | |
|---|---|---|---|
| WO | 2010049684 | A1 | 5/2010 |
| WO | 2015021216 | A1 | 2/2015 |
| WO | 2016022808 | A1 | 2/2016 |
| WO | 2016183084 | A1 | 11/2016 |

* cited by examiner

184

| | |
|---|---|
| TIP ID DATA | 188 |
| CURRENT $i_M^{MAX}$ | 190 |
| POTENTIAL $V_S^{MIN}$ | 192 |
| POTENTIAL $V_S^{MAX}$ | 194 |
| MIN FREQ. | 196 |
| MAX FREQ. | 198 |
| PID COEFFICIENTS | 204 |
| TIP USE HISTORY | 206 |

FIG. 6

ULTRASONIC SURGICAL TOOL SYSTEM INCLUDING A TIP CAPABLE OF SIMULTANEOUS LONGITUDINAL AND TORSIONAL MOVEMENT AND A CONSOLE CAPABLE OF APPLYING A DRIVE SIGNAL TO THE TIP SO THE TIP ENGAGES IN SUBSTANTIALLY TORSIONAL OSCILLATIONS

CROSS-REFERENCE TO RELATED APPLICATIONS

The present application is a National Stage of International Patent Application No. PCT/US2016/066635, filed on Dec. 14, 2016, which claims priority to and all the benefits of U.S. Provisional Patent Application No. 62/269,542, filed on Dec. 18, 2015, both of which are hereby expressly incorporated herein by reference in their entirety.

FIELD OF THE INVENTION

This invention relates generally to an ultrasonically driven surgical handpiece. More particularly, this invention relates to an ultrasonically driven handpiece that has plural modes of vibration and a method of driving the handpiece so the tip head undergoes vibrations that are essentially torsion vibrations.

BACKGROUND OF THE INVENTION

Ultrasonic surgical instruments are useful surgical instruments for performing certain medical and surgical procedures. Generally, an ultrasonic surgical tool includes a handpiece that contains at least one piezoelectric driver. A tip is mechanically coupled to the driver and extends forward from the housing or shell in which the driver is disposed. The tip has a head. The head is provided with features, often teeth, dimensioned to accomplish a specific medical/surgical task. An ultrasonic tool system also includes a control console. The control console supplies an AC drive signal to the driver. Upon the application of the drive signal to the driver, the driver cyclically expands and contracts. The expansion/contraction of the driver induces acoustic waves that propagate along the tip. The acoustic waves induce the tip, especially the head, into a back and forth motion. When the tip so moves, the tip is considered to be vibrating. The vibrating head of the tip is applied against tissue to perform a specific surgical or medical task. For example, some tip heads are applied against hard tissue. One form of hard tissue is bone. When this type of tip head is vibrated, the back and forth vibrations of the tip teeth, saw, remove, the adjacent hard tissue. Still other tip heads are designed to be placed against soft tissue.

Some ultrasonic tools remove tissue by inducing cavitation in the tissue and surrounding fluid. Cavitation occurs as a result of the tip head moving back and forth at or beyond a velocity that induces cavitation. Cavitation is the formation of small voids, cavities, in the tissue and surrounding fluid adjacent the tip. These cavities are very small zones of extremely low pressure. A pressure differential across the border between these cavities and the cells forming the adjacent tissue. Owing to the relatively large magnitude of this pressure differential, the cell walls burst. The bursting of these cell walls, removes, ablates, the cells forming the tissue. Some tips are formed with teeth that protrude laterally outwardly from the side of the tip head.

Physically, many tips include an elongated shaft. The proximal or rear end of the shaft is connected to the handpiece. A head, the tip head, is located at the distal end, the free end of the shaft. The head sometimes projects outwardly from the adjacent portion of the shaft. The head of an ultrasonic tip is often relatively small. Some heads have diameters of less than 1.0 cm. An ultrasonic tool removes tissue adjacent to where the head is applied. Owing to the relative small surface area of their heads, ultrasonic handpieces have proven to be useful tools for precisely removing both hard and soft tissue.

Other cutting implements used to selectively remove tissue are drill bits and burs. For a drill or bur to function, the implement is often rotated. Here, "rotation" is understood to mean repeating 360° movement around the longitudinal through the implement. The mechanical force of this rotation can, when opposed to a resistive force of the tissue, can cause the implement to jump out of the path of the cut. Still another undesirable effect of this rotation is that when the shaft of the implement invariably presses against tissue not intended for removal, the rotation can tear or otherwise damage the tissue. In contrast, neither the shaft nor the head of an ultrasonic tip rotates. This means when this type of implement is used in a procedure, the likelihood that the tissue could be damages as a result of the rotation of the tip are essentially eliminated.

Most tips are designed so that when the drive signal is applied, the tip head vibrates primarily in a single mode. Here the vibration mode is understood to be the path of travel along which the tip head travels. The majority of tips are designed to vibrate longitudinally. This means the heads move back and forth along an axis that is essentially in line with the proximal-to-distal longitudinal axis along the tip.

A problem can arise when a tip vibrates longitudinally. This type of tip, as discussed above, is designed so that when a side face of the tip head is applied against the tissue and vibrated, the teeth cut, resect, the tissue. Alternatively, or in combination with the cutting, the teeth foster cavitation that ablates the adjacent tissue. The problem occurs because sometimes the distal end of the shaft of the tip can vibrate at a velocity that induces cavitation in the tissue against which this end of the head is pressed. This cavitation can cause the unwanted ablation, removal, of tissue not targeted for removal. The challenges posed by reducing this unwanted tissue removal are further complicated by the fact that this removal is occurring at the distal end of the tip head. This location is one that is typically concealed from the sight of the practitioner. Consequently, it can be difficult for the practitioner to determine if owing to the placement of the tip, if this unwanted tissue ablation is occurring.

Some tips are available that vibrate in a mode other than a longitudinal mode. Some tips are designed so that their heads, when vibrated, engage in a torsional or rotation vibration. This means that that head, when excited into vibration, rotates around the tip longitudinal axis. Still other tips are designed to flex. This rotation is back and forth motion around an arc that subtends an angle less than 360°. This means that when the tip is excited, the longitudinal axis of the tip bends back and forth. The tip head moves with the bending, the flexing of the tip.

A characteristic integral with an ultrasonic handpiece is the mechanical resonant frequency of the handpiece. Here the handpiece is understood to mean both the drivers and the components of the handpiece coupled to the drivers including the tip. The mechanical resonant frequency is the frequency of these components at which, when the tip is vibrated at, the tip head undergoes vibratory motion of a peak range. For a tip that vibrates longitudinally, the peak range is understood to be the largest back and forth distance. For a tip that vibrates torsionally or flexural, the maximum range is understood to be the largest arc in a single phase of a vibratory cycle. Here peak range of motion is understood to be motion that is larger in magnitude than a motion that would occur if the drivers vibrate at a frequency slightly below or slightly above the resonant frequency.

Owing to their structure, some handpieces have plural mechanical resonant modes. This means this type of handpiece has plural frequencies at which, in comparison to adjacent frequencies, when the handpiece is vibrated, the tip head engages in a peak range of movement. Each mechanical resonant frequency is associated with an individual one of the mechanical resonant modes.

The Applicant's PCT Pub. No. WO 2015/021216 A1/US Pat. Pub. No. 10,016,209 B2, the contents of which are incorporated herein by reference, disclose a means for regulating the frequency of the drive signal, so this signal is at a frequency that as closely as possible matches the mechanical resonant frequency of the tip. Generally this process is performed by determining whether or not the below Equation, Equation (11), in PCT Pub. No. WO 2015/021216 A1 tests true:

$$-\mathrm{Re}\left\{\frac{\text{COMPLEX ELECTRICAL CURRENT DUE TO THE CAPACITANCE OF THE DRIVERS}}{\text{COMPLEX MECHANICAL EQUIVALENT OF CURRENT DUE TO THE MECHANICAL COMPONENTS OF THE HANDPiECE}}\right\} = 0 \qquad (1)$$

The frequency of the drive signal applied to the drivers functions as a variable of both the antecedent and the consequent of this ratio. PCT Pub. No. WO 2015/021216 A1 teaches regulating the drive signal frequency so the frequency is at a resonant frequency for a particular mechanical resonant mode of the handpiece. Typically this resonant frequency is for the mechanical resonant state of the handpiece which induces the vibrations of the largest peak range of movement of the tip head.

If the calculation to determine the above ratio yields a positive result, it is necessary to decrease the frequency of the drive signal so as to more closely match the resonant frequency of which results in the maximum desired vibrational movement. Typically the variables selected to calculate the ratio are selected to determine the frequency of the drive signal that will cause the tip to vibrate at the resonant frequency of the resonant state where longitudinal mode and torsional mode vibrations are of greatest magnitude.

In FIG. 1 frequency $f_1$, approximately 24.45 kHz, is the frequency associated with the first one of the mechanical resonant modes of a handpiece. This frequency is the resonant frequency of this resonant mode when the tip is in the unloaded state. A tip is in the unloaded state when the tip is vibrating in free space. When the tip is applied to tissue, the load of the tip increases above the free space load. This results in a change of the resonant frequency (or frequencies) of the mechanical resonant mode (or modes). The resonant frequency (or frequencies) of the tip may also change for other reasons. These reasons include changes in tip temperature or changes in the acoustic properties of the load applied to the tip. This is why PCT Pub. No. WO 2015/021216 A1 teaches one to continually evaluate whether or not Equation (1) tests true. As a result of the tip being applied to tissue the resonant frequency of the mechanical resonant mode changes. Thus, to ensure efficient operation of the system, including the tip, why PCT Pub. No. WO 2015/021216 A1 teaches one to, based on Equation (1), continually adjust the drive signal applied to the handpiece so the signal is at a frequency that as closely as possible matches the real time resonant frequency of the relevant mechanical resonant mode.

Some tips are now available that are designed to substantially reduce the undesirable effects caused by longitudinal movement of the tip shaft adjacent the tip head. Typically this tip is designed to simultaneously vibrate in two modes. Often this tip is designed to vibrate in both the longitudinal mode and the torsional mode. One tip capable of simultaneously vibrating in these two modes is the Long Micro Claw tip available from the Applicant, Stryker Corporation, of Kalamazoo, Mich. The structure of this tip is disclosed in U.S. Pat. No. 6,955,680, COUPLING VIBRATION ULTRASONIC HAND PIECE, the contents of which is explicitly incorporated by reference. In brief, this type of tip has features that breakdown the longitudinal vibrations that are transmitted from the drivers are broken down into two components. Specifically, these features breakdown the vibrations so that each vibration has a longitudinal component, a longitudinal mode vibration, and a torsional component, a torsional mode vibration.

The tip head vibrations are vibrations that equal the sum of the longitudinal mode vibrations and sum of the torsional mode vibrations.

The above-described tip has, in the relevant frequency range, two mechanical resonant modes. In FIG. 1, frequency $f_1$ is the resonant frequency associated with the first mechanical resonant mode. Frequency $f_2$, 25.32 kHz is the resonant frequency associated with the second mechanical resonant mode. When the tip is vibrated at the mechanical resonant frequency associated with the first mechanical resonant mode, the distal portion of the tip undergoes a both a longitudinal movement and a torsional movement that are at peak range in comparison the ranges of movement when the drive signal is either slightly below or slightly above this resonant frequency. When the tip is vibrated at the mechanical resonant frequency associated with the second mechanical resonant mode, the distal portion of the tip undergoes both a longitudinal movement and a torsional movement that are at peak range in comparison to the range of movement when the drive signal is either slightly below or above this resonant frequency. For tips to which a drive signal of approximately 25 kHz is applied, the definition of "slightly below" may be a frequency of 100 to 300 Hz below the mechanical resonant frequency. For this type of tip, the definition of "slightly above" may be a frequency of 100 to 300 Hz above the mechanical resonant frequency.

Often the peak range of motion produced when the tip is vibrated at one of the mechanical resonant modes is a larger range of movement than the peak range of movement when the tip is vibrated at the frequency associated with the other mechanical resonant mode. The above-mentioned incorporated by reference PCT Pub. No. WO 2015/021216 A1 teaches one apply source a drive signal that causes the tip to vibrate at the resonant frequency of the mechanical resonant mode at which the peak range of motion has the largest magnitude. In FIG. 1 this is frequency $f_1$.

The Applicant's PCT App. No. PCT/US2015/044023, published as WO 2016/022808 A1/US Pat. Pub. No. 10,561,435 B2, the contents of which are incorporated herein by reference discloses an alternative system for regulating the application of the drive signal applied to the handpiece. This document is directed to a system that discloses how a drive signal that has plural components can be applied to the handpiece. A first component of the drive signal has a potential and is at frequency associated with the first mechanical resonant mode, frequency $f_1$ in FIG. 1. A second component of the drive signal has a potential and is at the frequency associated with the second mechanical resonant mode. This is frequency $f_2$ in FIG. 1. By adjusting potentials and frequencies of the individual components of the drive signal the magnitude of sum of the longitudinal components of the vibrations associated with the two mechanical resonant modes can be adjusted. The adjustment of the potentials of the individual components of the drive signal also sets the magnitude of the sum of the torsional components of the vibrations of the two resonant states. By adjusting these individual vibration components the tip can be vibrated in such a way that the tip head engages in a path of travel that can be considered non-linear. Here, a non-linear path of travel is a path of travel such that when a single point on a tip head engages in a single back and forth vibratory cycle, in a first phase of the cycle the point transits over a first set of points in a space, in the second phase, the return phase, the tip transits over a second set of points in space. This second set of points is different from the first set of points. In one instance the path of travel in a single cycle is essentially elliptical.

A benefit of driving the tip in a non-linear path of travel is that in a first phase, the tooth strikes the bone and then in the next phase of movement rubs against the bone. During the striking phase of tip tooth movement, the tip fractures the bone to remove the desired quantity of bone. During the phase of movement when the tooth rubs against the bone, the tooth clears away the debris just formed as result of the tooth striking phase. The clearing away of these debris results in a like reduction of the extent to which the presence of the debris during the next vibratory cycle adversely affects the bone cutting process.

For the reasons set forth above, it is useful to apply a drive signal to an ultrasonic handpiece that causes the tip to undergo simultaneous vibrations in two vibratory modes, longitudinal and torsional.

Nevertheless, even a tip designed driven to engage both torsional mode vibrations and longitudinal mode vibrations will along the shaft of the tip undergo some longitudinal movement. For the reasons set forth above, this movement can result in unwanted cavitation adjacent the distal end of the tip head and, by extension, unwanted tissue ablation. Accordingly, there are still some situations where it would be best if a drive signal could be applied to the handpiece so that the tip is forced into what vibrations that are substantially torsional and that have a minimal, if any, longitudinal component.

SUMMARY OF THE INVENTION

This invention is related to a new and useful ultrasonic surgical tool system. The system of this invention includes a handpiece with a tip and complementary control system for supplying a drive signal that vibrates the tip. Collectively the console and tip are arranged so that when the drive signal is applied to the tip the tip engages in motion that is primarily in the torsional mode.

The system of this invention includes a handpiece with a tip. The tip of this invention has features that convert a component of the longitudinal vibrations into torsional vibrations.

This invention is based on the principle that, owing to the characteristics of the mechanical components forming the handpiece, including the tip, the handpiece has between the resonant frequencies of the first and second mechanical resonant modes a longitudinal mechanical cancellation frequency. When a drive signal is applied to the handpiece drivers at this frequency, the mechanical components of the handpiece are excited into simultaneously inducing both first and second mechanical resonant mode vibrations in the tip. A further principle upon which this invention is based is that when the mechanical components are excited into vibrating simultaneously in the two mechanical resonant modes, the longitudinal vibrations associated with the resonant modes are out of phase with each other and the torsional vibrations are in phase.

As a result of the handpiece being so vibrated, since the longitudinal vibrations of the individual modes are out of phase, these vibrations cancel each other out. Since the torsional vibrations of the individual modes are in phase, the tip, more particularly, the head and the adjacent section of the shaft, engage in appreciable torsional vibrations. Thus the tip head of this invention undergoes substantial torsional vibrations while the head and the adjacent section of the shaft undergo minimal, if any longitudinal vibrations.

This invention is directed to a system that, by monitoring the characteristics of the drive signal applied to the handpiece, continually adjusts characteristics of the drive signal. More particularly the frequency of the drive signal is continually adjusted to ensure that this signal, as closely as possible, equals the longitudinal mechanical cancellation frequency of the handpiece.

This continual monitoring of the drive signal and subsequent adjustment of the frequency of this signal is necessary because, as the load applied to the mechanical components of the handpiece change, the longitudinal mechanical cancellation frequency likewise shifts.

BRIEF DESCRIPTION OF THE DRAWINGS

The invention is pointed out with particularity in the claims. The above and other features and benefits of the invention are further understood from the following Detailed Description taken in conjunction with the accompanying drawings in which:

FIG. 6 depicts types of data stored in the memory integral with the tool tip;

DETAILED DESCRIPTION

I. System Overview and Hardware

An ultrasonic tool system 30 that includes the features of this invention is now generally described by reference to FIGS. 2 and 3. System 30 includes a handpiece 32. A tip 142 is attached to and extends distally forward from the handpiece 32. ("Distal" is understood to mean away from the practitioner, towards the site to which the handpiece is applied. "Proximal" is understood to mean towards the practitioner holding the handpiece, away from the site to which the handpiece is applied.) Tip 142 is the component of system 30 that is applied to tissue to perform the desired medical/surgical procedure. System 30 also includes a control console 230. Control console 230 sources a drive signal that is applied to the handpiece 32. In response to application of the drive signal, handpiece 32 causes tip 142 to vibrate.

Figure 2:
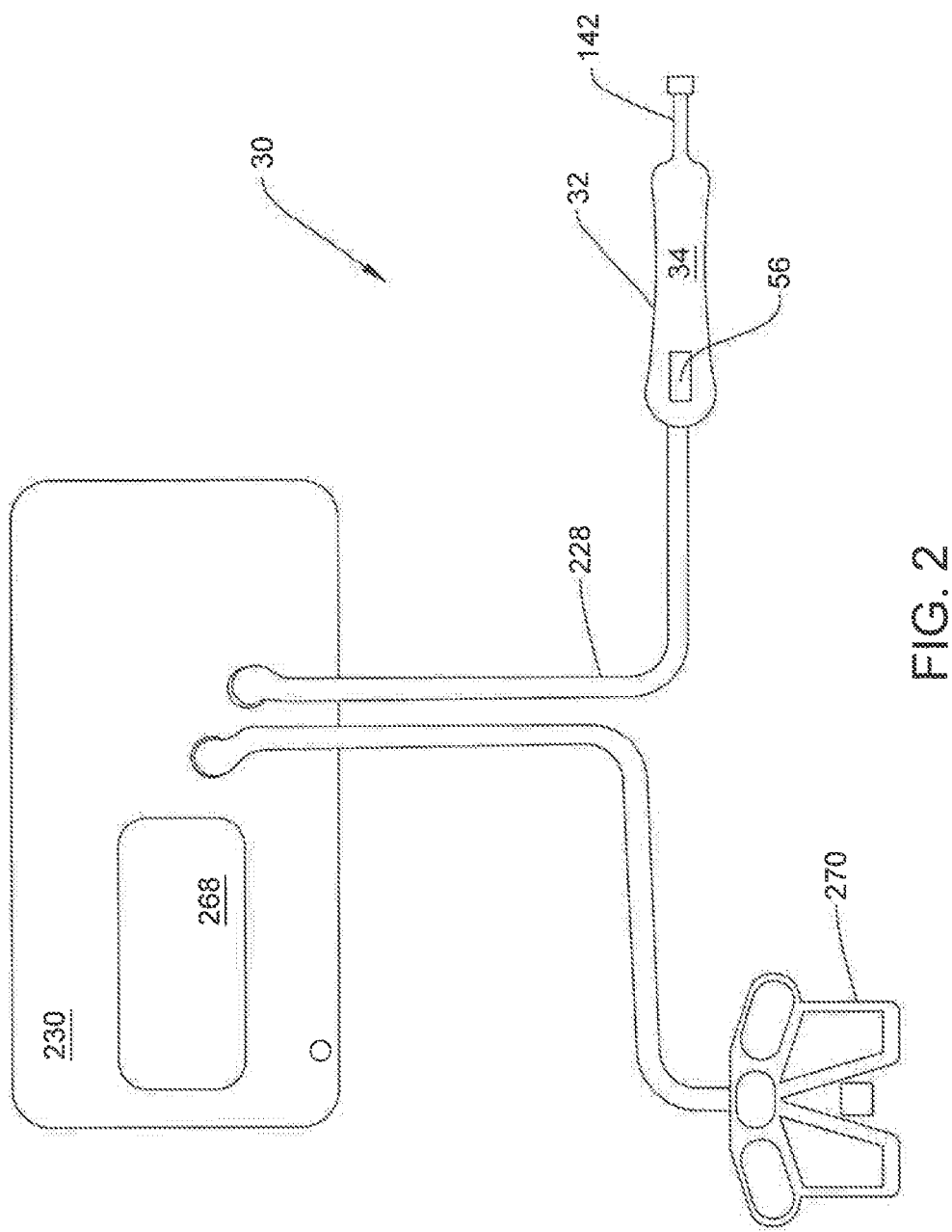
FIG. 2 depicts the basic components of an ultrasonic tool system that includes the features of this invention.

Handpiece 32 includes a body or shell 34, seen only in FIG. 2. From FIGS. 3 and 4 it can be seen that one or more vibrating piezoelectric drivers 36 (four shown) are disposed inside the shell 34. Each driver 36 is formed from material that, when a current is applied to the driver, undergoes a momentary expansion or contraction. The driver expansions/contractions are on the longitudinal axis of a driver 36, the axis that extends between the proximally and distally directed faces of the driver. A pair of leads 38 extends away from each driver 36. Leads 38 are attached to the opposed proximally and distally directed faces of the drivers. Many, but not all, handpieces 32 include drivers 36 that are disc shaped. Drivers 36 are arranged end to end in a stack. Leads 38 are the components of system 30 over which the drive signal is applied to the drivers 36. Optional insulating discs 40, one shown, are disposed between adjacent drivers 36. In FIG. 3 drivers 36 and the insulating disc 40 are shown spaced apart from each other. This is for ease of illustrating the components. In practice, drivers 36 and insulating discs 40 tightly abut.

A post 44 extends longitudinally through the drivers 36, leads 38 and insulting discs. The post 44 extends through the drivers 36, leads 38, and insulating discs 40 and along the collinear longitudinal axes of these components. Not seen are through bores internal to the drivers 36, leads 38 and insulating discs 40 through which the post 44 extends. Post 44 projects outwardly of both the most proximally located driver 36 and the most distally located driver.

A proximal end mass 46 is located adjacent and abuts the proximally directed face of the most proximally located driver 36. Mass 46 is attached to the proximal end section of post 44. If post 44 is threaded, mass 36 may be a nut.

Figure 3:
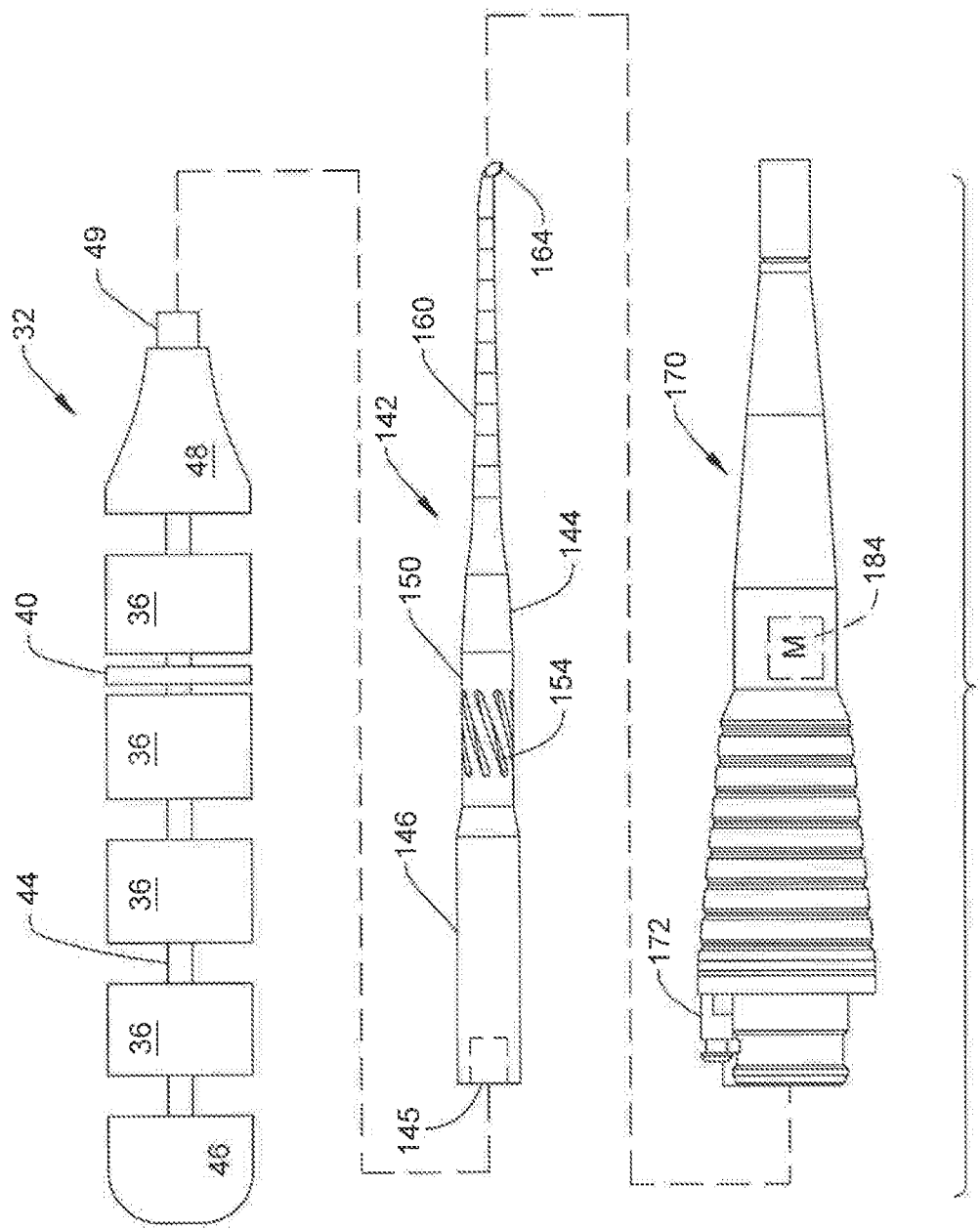
FIG. 3 is a diagrammatic and exploded depiction of the mechanical components of the tool, the handpiece, tip and sleeve of the system.

A horn 48, seen in FIG. 3, extends forward from the distally directed face of the most distally located driver 36. Horn 48 has a base with a diameter approximately equal to the diameter of the drivers 36. Extending distally forward from the drivers 36, the diameter of the horn 48 decreases. The exposed distal end section of post 44 is affixed to the horn 48. In many versions of the invention, post 44 and horn 48 are a single piece unit. Handpiece 32 is constructed so that the stack of drivers 36 and insulating discs is compressed between proximal mass 46 and horn 48.

Also disposed in handpiece shell 34 is a handpiece memory 56. Memory 56 contains data used to regulate the operation of the handpiece 32 and tip 142. Memory 56 may take the form of an EPROM, an EEPROM or an RFID tag. The structure of the memory is not part of the invention. For purposes of illustration handpiece memory 56 is an RFID tag. A coil 54 is shown connected to memory 56. Coil 54 is the component associated with the handpiece over which the control console 230 reads from and writes to the handpiece memory 56.

Figure 5:
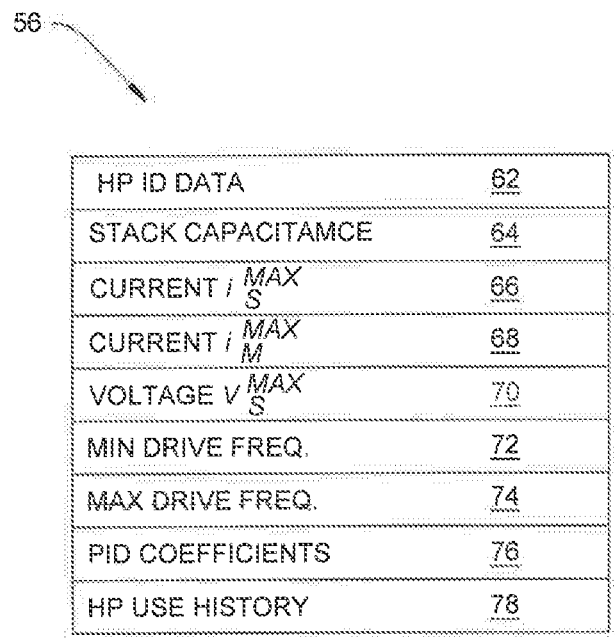
FIG. 5 depicts types of data stored in the memory internal to the handpiece.

FIG. 5 illustrates types of data stored in the handpiece memory 56. These data, as represented by field 62, include data identifying the handpiece 32. These data are useful for verifying that the console 230 is able to apply a drive signal to the handpiece. Data in field 62 may also indicate the type of information regarding the handpiece that is presented on the console display 268. Other data in the handpiece memory 56 are used to regulate the sourcing of drive signals to the drivers 36. While the use of these data are discussed below, the types of data are now described. Field 64 contains data indicating the capacitance $C_O$, the capacitance of the stack of drivers 36. Driver capacitance can be determined by analysis during the process of assembling the handpiece 34. Often the sum of the capacitance of the drivers is between 500 to 5000 pF. Data regarding the maximum current that should be applied to the handpiece 36, current $i_S^{MAX}$, are contained in a field 66. Current $i_S^{MAX}$ is often less than 1 Amp peak and more often 0.5 Amp peak or smaller. Field 68 contains data indicating maximum below discussed mechanical equivalent of current, $i_M^{MAX}$, that should flow through the below discussed mechanical components of the handpiece. Current $i_M^{MAX}$ is typically 0.25 Amps peak or less. The maximum potential of the drive signal, voltage $V_S^{MAX}$, are stored in field 70. Voltage $V_S^{MAX}$ is often 1500 Volts AC peak.

Also stored in handpiece memory 56 are data indicating the minimum and maximum frequencies of the drive signal that should be applied to handpiece 32. The minimum frequency, stored in field 72, is typically the minimum frequency of the drive signal that can be supplied by the control console. The maximum frequency of the drive signal, stored in field 74, is typically between 5 kHz and 40 kHz greater than the minimum frequency.

Field 76 contains coefficients for controlling the control signals output by controller 96. PID control loops are used to establish the final levels for each of these signals. Field 76 contains the coefficients for each of these control loops. It should be understood that the data in fields 62, 66, 68, 70, 72, 74 and 76, like the data in field 64, are stored in the handpiece memory 56 as part of the process of assembling the handpiece.

Handpiece memory 56 also contains field 78 as a use history field. Control console 230, during use of the handpiece 32, writes data into field 128 so as to provide a log of the operation of the handpiece.

Returning to FIG. 4, it can be seen that also shown internal to the handpiece 32 are two conductors 132. Conductors 132 extend from coil 54 to the distal end of the handpiece. The conductors 132 are connected to a second coil, coil 134, also disposed in the handpiece 32.

Tip 142 extends forward from the handpiece horn 48. The tip 142 has a generally cylindrical shaft 144. In some, but not all versions of the invention, shaft 144 has plural sections each with a different cross sectional diameter. In the illustrated version of the invention, tip shaft 144 has a proximal section 146. Shaft proximal section 146 is formed with coupling features designed to facilitate the removable coupling of the tip to handpiece 32. In one version of the invention, the handpiece coupling feature is a boss 49 that extends forward from horn 48. The outer surface of the boss 49 is formed with threading (not illustrated). The tip coupling feature is a closed end bore 145 that extends inwardly from the proximal end of the shaft 144 partially through the shaft proximal section 145. Bore 145 is provided with threading (not illustrated) designed to engage the threaded boss integral with the handpiece horn 48.

In the depicted versions of the invention, shaft 144 has a middle section 150 that extends forward from the shaft proximal section 146. Middle section 150 has a diameter less than that of the proximal section 146. The depicted shaft 144 has a distal section 160. Shaft distal section 160 has a diameter less than that of the middle section 150. Not identified are the tapered transition sections of the shaft 144. One transition section is between the proximal section 146 and the middle section 150. A second transition section is between the middle section 150 and the distal section 160. The distal section of the shaft has its own slight taper such that as the section 160 extends distally the diameter of the shaft slightly decreases.

A head 164 is the most distal portion of tip 142. Head 164 is located immediately forward of the shaft distal section 160. Head 164 is sometimes formed with teeth or flutes (not illustrated). Tip head 164 is the portion of system 30 pressed against tissue to perform a desired procedure. The teeth or flutes are designed so that when the head 164 moves, the teeth or flute bear against tissue. As a consequence of the movement of the head, the teeth or flutes remove tissue. The geometry of the tip teeth or flutes is not part of the present invention.

Handpiece 32 is generally designed so that the back and forth movement of the drivers induce a like vibrating motion in the tip 142. These are longitudinal vibrations in that the motion is back and forth along the longitudinal axis of the tip and, more particularly, the shaft. A tip 142 of this invention is further provided with features that convert the proximal to distal vibratory motion applied to the proximal end of the shaft 144 into two vibratory motions. In the depicted tip 142 these features are helical grooves 154 that extend inwardly from the outer surface of shaft middle section 150. Owing to the presence of grooves 154, a fraction of the longitudinal motion applied to the shaft proximal section 146 into motion that causes the more distal sections of the tip to, in addition to vibrating longitudinally, vibrate rotationally. Rotational vibration is understood to mean the vibration of the shaft and tip in an arc that extends around the longitudinal axis of the shaft 144.

A sleeve 170 is disposed around tip shaft 144. Sleeve 170 is formed of plastic. The proximal end the sleeve is formed with features that facilitate the releasable coupling of the sleeve to the distal end of the handpiece shell 34. The components forming system 30 are formed so that sleeve is spaced radially away from tip shaft 144 and longitudinally away from tip head 160. More specifically the components are dimensioned so that during the normal vibration of the tip, the tip does not abut the sleeve.

While not part of the present invention, it can be seen that sleeve 170 is often formed with a fitting 172. Fitting 172 is formed to receive an irrigation line. During use of system 30, irrigating fluid is often flowed into the sleeve 170. The fluid flows around through the gap between the tip 142 and the sleeve 170 and out the open distal end of the sleeve. Handpiece post 44 and the tip 142 are formed with contiguous bores (bores not illustrated). During a procedure, suction is drawn through these bores. The suction draws from the site to which tip head 164 is applied the irrigating fluid as well as debris formed by the procedure that are entrained in the fluid. The suction also draws tissue towards the tip head 164. This drawing of the tissue towards the tip head 164 enhances the cutting of the tissue by the tip head.

Disposed inside the sleeve is a tip memory 184, seen as a dashed rectangle in FIG. 3. Memory 184 is referred to as the tip memory because, even though the memory is disposed in sleeve 170, the memory is used to control the operation of the tip 142. Further, tip 142 and sleeve 170 are typically distributed together as a single package. Tip 142 is typically initially first coupled to the handpiece 32. After the tip 142 is in place, the sleeve 170 is fitted to the handpiece. Tip memory 184 is typically the same type of memory as handpiece memory 56. Accordingly, in the illustrated version of the invention, tip memory 184 is an RFID tag. A coil 182, seen only in FIG. 4, embedded in sleeve 170 is connected to the input pins of the tip memory 172. The components forming system 30 are constructed so that when the sleeve 170 is fitted to the handpiece 32, handpiece coil 134 and coil 182 are able to engage in inductive signal exchange.

FIG. 6 depicts the type of data contained in tip memory 184. As represented by field 188, these data include a tip identification field. The data in field 188 identifies the tip and is analogous to the data identifying the handpiece in handpiece memory identification field 112. In field 190 data are stored indicating the maximum total mechanical equivalent of current, $i_M^{MAX}$, that should go through the mechanical components of the handpiece when the specific tip 142. Field 192 contains data indicating a minimum voltage $V_S^{MIN}$, of the drive signal that should be applied to the handpiece drivers used to vibrate the tip. Field 193 contains data indicating a maximum voltage, $V_S^{MAX}$, of the drive signal that should be applied to the handpiece drivers used to vibrate the tip.

Field 194 contains data defining a lowest possible frequency (MIN MRM FREQ.) for one of the mechanical resonant modes. Field 195 contains data defining a highest possible frequency (MAX MRM FREQ.) for the mechanical resonant mode for which filed 195 defines the lowest possible frequency. Typically fields 194 and 195 contain data defining the range of frequencies for the first mechanical resonant mode. This range of frequencies is a function of the difference between the frequencies of the first and second resonant modes. For example, if the difference between the frequencies of the two mechanical resonant modes is 2000 Hz or more, the range of frequencies contained in the data of fields 194 and 195 may be 1000 Hz. More often, the range of frequencies around the mechanical resonant frequency defined by data in in fields 194 and 195 is 400 Hz or less. In more preferred versions of the invention, the frequency range around the mechanical resonant frequency is 100 Hz or less.

Field 196 contains data defining a lowest possible frequency (MIN LCM FREQ.) of a below discussed longitudinal mechanical cancellation frequency for the tip 142. Field 198 contains data defining a highest possible frequency (MAX LCM FREQ.) for the longitudinal mechanical cancellation frequency. The frequency range defined by the data in fields 196 and 198 is also a function of the resonant frequencies of the two mechanical resonant modes. This frequency range is typically centered on the longitudinal mechanical cancelation frequency of the tip when the tip is in the no load state. The frequency range may partially overlap the frequency range associated with the mechanical resonant mode at which the tip may be driven. The frequency range of the operation of the tip around the longitudinal mechanical cancelation frequency should not though extend to the resonant frequency of the mechanical resonant mode at which the tip can be driven.

A PID coefficient field 204 contains control coefficients for the control signals that for the tip may be more specific than the data in handpiece memory PID coefficient field 76. Tip memory 184 also contains a tip use history field 206. During operation of system 30, the control console 230 writes data to field 206 regarding use of the tip 142

Figure 4:
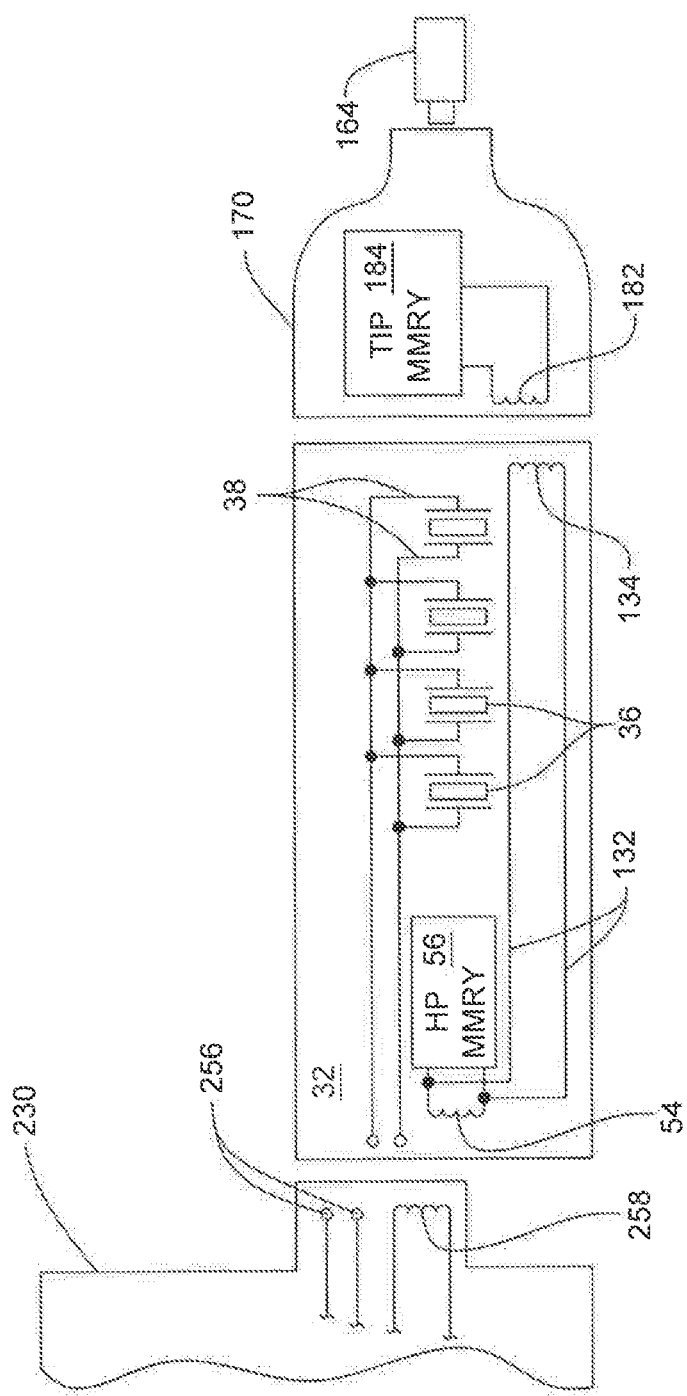
FIG. 4 is a block diagram depicting the electrical components of the handpiece and tip and how these components are connected to the control console.
Figure 7:
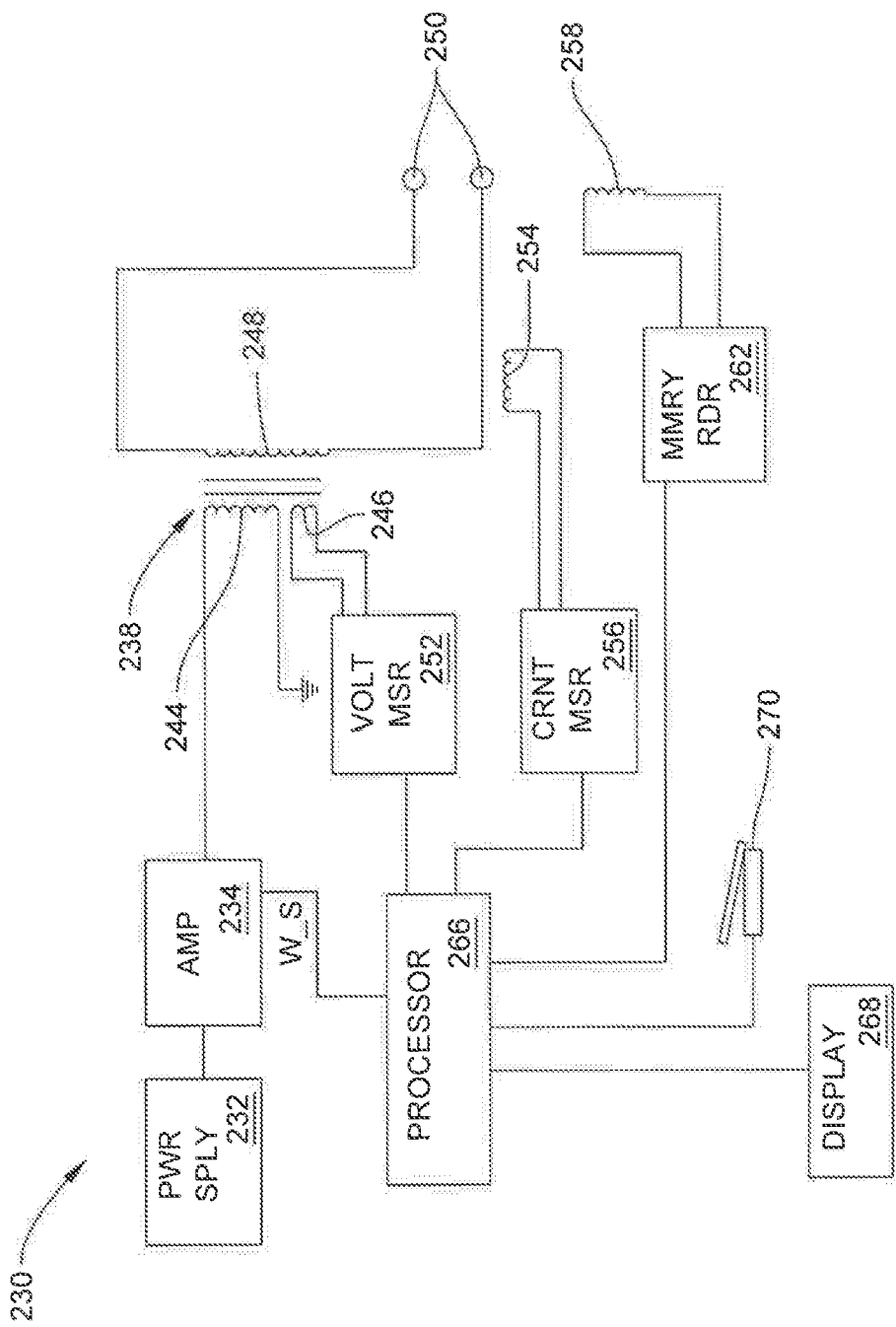
FIG. 7 is a block diagram of the electrical components of the control console and handpiece components of the system of this invention.

Control console 230, now described with respect to FIGS. 2, 4 and 7, supplies the drive signal to handpiece 32 that results in the vibration of tip 142. These components include a power supply 232. Power supply 232 outputs a constant voltage signal typically between 1 and 250 VDC. In many versions of the invention, the maximum potential of the voltage output by power supply 232 is 200 VDC or less. The voltage produced by power supply 232 is applied to a variable gain amplifier 234. A control signal, specifically a WAVEFORM_SET (W_S) signal, is applied to amplifier 234. The WAVEFORM_SET signal varies in both frequency and amplitude. The WAVEFORM_SET frequency is thus used to vary the gain and frequency of the signal produced by the amplifier 234 so the amplifier produces an output signal that varies in both potential and frequency. One such amplifier that can be incorporated into control console 230 is disclosed in U.S. Prov. Pat. App. No. 62/159,672 the contents of which are disclosed in the incorporated by reference PCT Pub. WO 2016/183084/US Pat. Pub. No. 10,449,570 B2. More particularly, amplifier 234 is capable of outputting a signal with a frequency of between 10 kHz and 100 kHz. Often the signal has a minimum frequency of 20 kHz and a maximum frequency of 40 kHz.

The output signal from amplifier 234 is applied to the primary winding 244 of a transformer 238, also part of the control console 230. The voltage present across the secondary winding 248 of the transformer 238 is the drive signal applied to the handpiece drivers 36. This voltage is typically a maximum of 1500 volts AC peak. The drive signal is applied in parallel across the drivers 36.

Transformer 238 includes a tickler coil 246. The voltage present across tickler coil 246 is applied to a voltage measuring circuit 252. Based on the signal across tickler coil 246, circuit 252 produces a signal representative of the potential and phase of voltage $V_S$, the voltage of the drive signal applied to the handpiece 32. A coil 254, also disposed in control console 230, is located in close proximity to one of the conductors that extends from the transformer secondary winding 248. The signal across coil 254 is applied to a current measuring circuit 256. Circuit 256 produces a signal representative of the magnitude and phase of current $i_S$, the current of the drive signal sourced to the handpiece 32.

The drive signal present across transformer secondary winding 248 is present at two conductive contacts 250 attached to a socket integral with the control console (socket not illustrated).

The drive signal is applied to the handpiece drivers by a cable 228 seen only in FIG. 2. In many constructions of system 30, handpiece 30 and cable 228 are a single unit. Cable 228 is connected to the control console socket in which contacts 250 are located.

In versions of the invention wherein the handpiece 32 and cable 228 are a single unit, handpiece coil 54 is disposed in the plug integral with the cable. Disposed in the console socket is a complementary coil 258. The components forming the system are configured so that when the plug integral with cable 228 is seated in the handpiece socket, coils 54 and 258 are able to inductively exchange signals.

The signals representative of the drive signal voltage $V_S$ and current $i_S$ are sourced to the handpiece are applied to a processor 266 also internal to the control console 230. Control console 230 also includes a memory reader 262. Memory reader 262 is connected at one end to console coil 258 and at an opposed end to processor 266. The memory reader 262 converts the signals present across the coil 258 into data signals processor 266 is able to read. Memory reader 262 also, in response to signals output by the processor 266, output signals across coil 258 that cause the coil to output signals that result in the writing of data to the handpiece memory 52 and tip memory 184. The structure of memory reader 262 complements the handpiece memory 102. Thus, memory reader 262 can be: an assembly capable of reading data in an EPROM or EEPROM or an assembly capable of interrogating and reading data from an RFID tag.

Processor 266 generates the WAVEFORM_SET signal that is applied to amplifier 234. The processor 266 thus sets the characteristics of the drive signal output by the control console 230 and applied to the handpiece 32. The characteristics of the drive signal set by processor 266 are the voltage and frequency of the drive signal. Processor 266 determines these characteristics as a function of the characteristics of the handpiece 32 and the characteristics of the tip 134. Processor 266 also determines the drive signal as a function of the acquired measurements of voltage $V_s$, and current $i_s$.

A display 268 is built into control console 230. The image on display 268 is shown as being generated by processor 266. Information depicted on display 268 includes: information identifying the handpiece 32 and the tip; and information describing characteristics of the operating state of the system. Display 268 is often a touch screen display. Processor 266 causes images of buttons to be presented on the display. By depressing the buttons, the practitioner is able to set what he/she desires as specific operating characteristics of the system 30.

In addition to the buttons presented on the display 268, there is typically at least one on on/off switch associated with the control console. In FIGS. 2 and 7, this on/off switch is represented by a footswitch 270. Footswitch 270 is configured to generate a signal that varies with the extent to which the switch is depressed. The signal is sourced to processor 266. Based on the state of the signal sourced by the footswitch 270, processor 266 regulates the generation of the drive signal so as to control both whether or not the tip vibrates and the magnitude of the tip head vibrations.

II. Fundamentals of Operation

Figure 8:
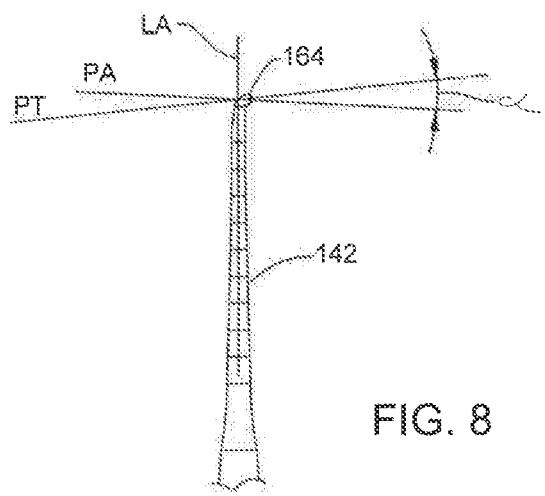
FIG. 8 represents in two dimensions, the path of travel of a point of the tip head around the longitudinal axis when the tip is vibrated according to this invention.

System 30 of this invention is designed so that the control console 230 outputs a drive signal that results in the tip head 164 moving along a path of travel that can be considered substantially torsional. Here a substantially torsional path of travel is understood to be a path of travel, line PT of FIG. 8, for a point on the tip head 164, is at an acute angle α that is 30° or less, preferably 15° or less and, more preferably, 8° or less relative line PA. Line PA is understood to be perpendicular to line LA, the longitudinal axis through tip 142. Line LA and line PA are understood to be in the plane of FIG. 8. In FIG. 8, line PT represents in two dimensions, the path of travel of the single point of the tip head. Thus to the left of where lines LA, PA and PT intersect, line PT extends below line PA and out of the plane of FIG. 8. To the right of where lines LA, PA and PT intersect, line PT extends above line PA into the plane of FIG. 8. Thus the path of travel around which a point on head 164 would move if the head engaged in simultaneously torsional and longitudinal movement is one in which the point would both rotate partially around line PA and move up and down along a longitudinal path of travel parallel to line LA. Under perfect conditions, the tip head 164 engages in torsional motion and does not engage in any longitudinal motion. If the tip head 164 engages in this type of motion it is understood that the acute angle between and line PA and line PT would be 0°.

A primary principle upon which operation of system 30 is based is that, owing to the presence of grooves 154, the features that convert the longitudinal motion of the tip into torsional motion, the handpiece, including the tip, have first and second mechanical resonant modes that have resonant frequencies that are spaced apart from each other. For many versions of the system to operate where the drive signals are in the range of 20 kHz to 40 kHz the resonant frequencies of the two mechanical resonant modes should be spaced apart by at least 250 Hz. In more preferred versions of the invention, these resonant frequencies are spaced apart by at least 500 Hz.

A first corollary principle upon which operation of the system is based is that when a drive signal is applied to the handpiece drivers 36 that is at the resonant frequency associated with the first mechanical resonant mode, the tip head undergoes a combined longitudinal and torsional vibration at this frequency. The tip head does not engage in appreciable vibratory motion that can be associated with the second mechanical resonant mode.

A second corollary principle upon which operation of the system is based is that when a drive signal is applied to the handpiece drivers 36 that is at the resonant frequency associated with the second mechanical resonant mode, the tip head undergoes a combined longitudinal and torsional vibration at this frequency. The tip head does not engage in appreciable vibratory motion that can be associated with the first mechanical resonant mode.

Figure 9:
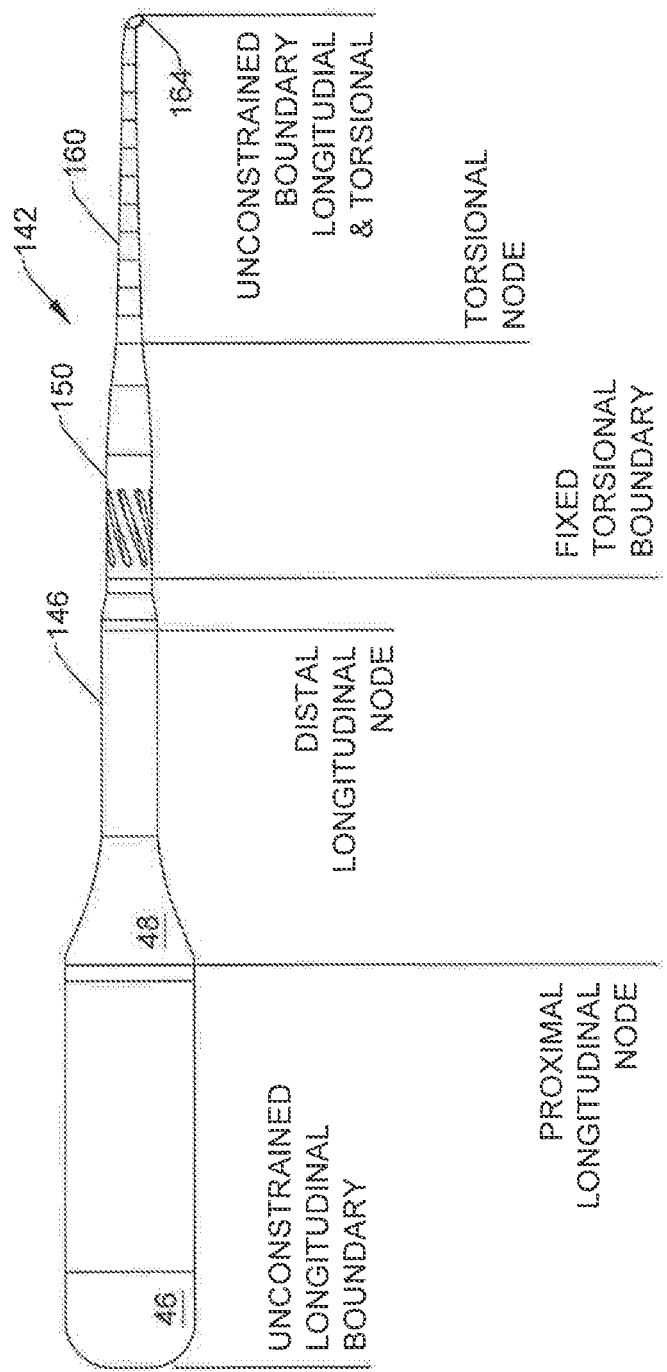
FIG. 9 is a diagrammatic indication of the location of the boundaries and nodes associated with longitudinal and torsional vibrations of the handpiece, including the tip.

The boundaries and nodes of the vibrations associated with the handpiece are now described with reference to FIG. 9. The proximal end of the proximal end mass 46 represents the proximal unconstrained boundary of the longitudinal vibrations of the handpiece. Here the handpiece is understood to include the tip 142. Distally forward of the proximal unconstrained longitudinal boundary there is a first longitudinal node, the proximal longitudinal node. This node may be located adjacent the distal most driver 36. Forward of the proximal longitudinal node there is the second longitudinal node, the distal longitudinal node. This node is located in the tip 142 at a location proximal to the helical grooves 154. At the longitudinal nodes, the longitudinal expansion/contraction waves the drivers induce in the handpiece neither expand nor contract the handpiece or tip. On the opposed sides of each longitudinal nodes, the acoustic waves generated by the drivers induce opposed expanding and contracting movements of the handpiece. Thus, when during each resonant mode of the handpiece, the drivers induce expansion of the handpiece between proximal unconstrained boundary and the proximal longitudinal node, there is contraction between to the two longitudinal nodes and expansion distal to the distal longitudinal node. Similarly, when, for a resonant mode, the drivers induce contraction between the proximal unconstrained boundary and the proximal longitudinal node, the handpiece undergoes expansion between the longitudinal nodes and, distal to the distal longitudinal node, contraction.

At a location distal to the distal longitudinal node and proximal to grooves 154, the handpiece has a fixed torsional boundary. Distal to this location, owing to the presence of grooves 154, a fraction of each longitudinal expansion/compression wave that passes through the tip, is converted into motion that twists the tip, induces a torsional motion. Forward of the grooves 154, there is a torsional node. At the torsional node the tip does not engage in any torsional motion. Distal to the torsional node, the tip twists in a direction opposite the direction in which the section of the tip between the fixed torsional plane and the torsional node twists.

The distal end of the tip head 164 is the unconstrained boundary for both the longitudinal and torsional vibrations of the handpiece. This boundary is an unconstrained boundary because the tip head is not attached to a fixed object that constrains the motion of the tip. This is why, when a drive signal is applied to the handpiece, the vibratory motions transmitted through the tip shaft 144 to the tip head 164 induce vibratory movement of the tip head.

When a drive signal is applied to the handpiece drivers at a frequency between the first and second mechanical resonant modes, the mechanical components of the handpiece are driven to simultaneously engage in the plural vibrations associated with each of the first and second mechanical resonant modes. Thus, when a drive signal is applied to the handpiece drivers at a frequency between the resonant frequencies of the first and second mechanical resonant modes, the force the drivers 36 apply to the rest of the handpiece induces longitudinal expansions/contractions that have a component associated with the first mechanical resonant mode and a component associated with the second resonant mode. It is further understood longitudinal vibrations associated with the second mechanical resonant mode are out of phase with the longitudinal vibrations associated with the first mechanical resonant mode.

Similarly, when a drive signal is applied to the handpiece drivers at the frequency between the resonant frequencies of the first and second mechanical modes, the mechanical components of the tip 142 distal to grooves 154 engage in torsional vibrations that have a component associated with the first mechanical resonant mode and a component associated with the second mechanical resonant mode. It is further understood that the torsional vibrations of the tip associated with the second resonant mode are in phase with the torsional vibrations of the tip associated with the first resonant mode. This means when the tip engages in a longitudinally contracting (or expanding) motion due to being vibrated in the second mechanical resonant mode, the tip is forced into torsional motion in the same direction as when the tip is engages in a longitudinal expanding (or contracting) motion due to being vibrated in the first mechanical resonant mode.

Figure 1:
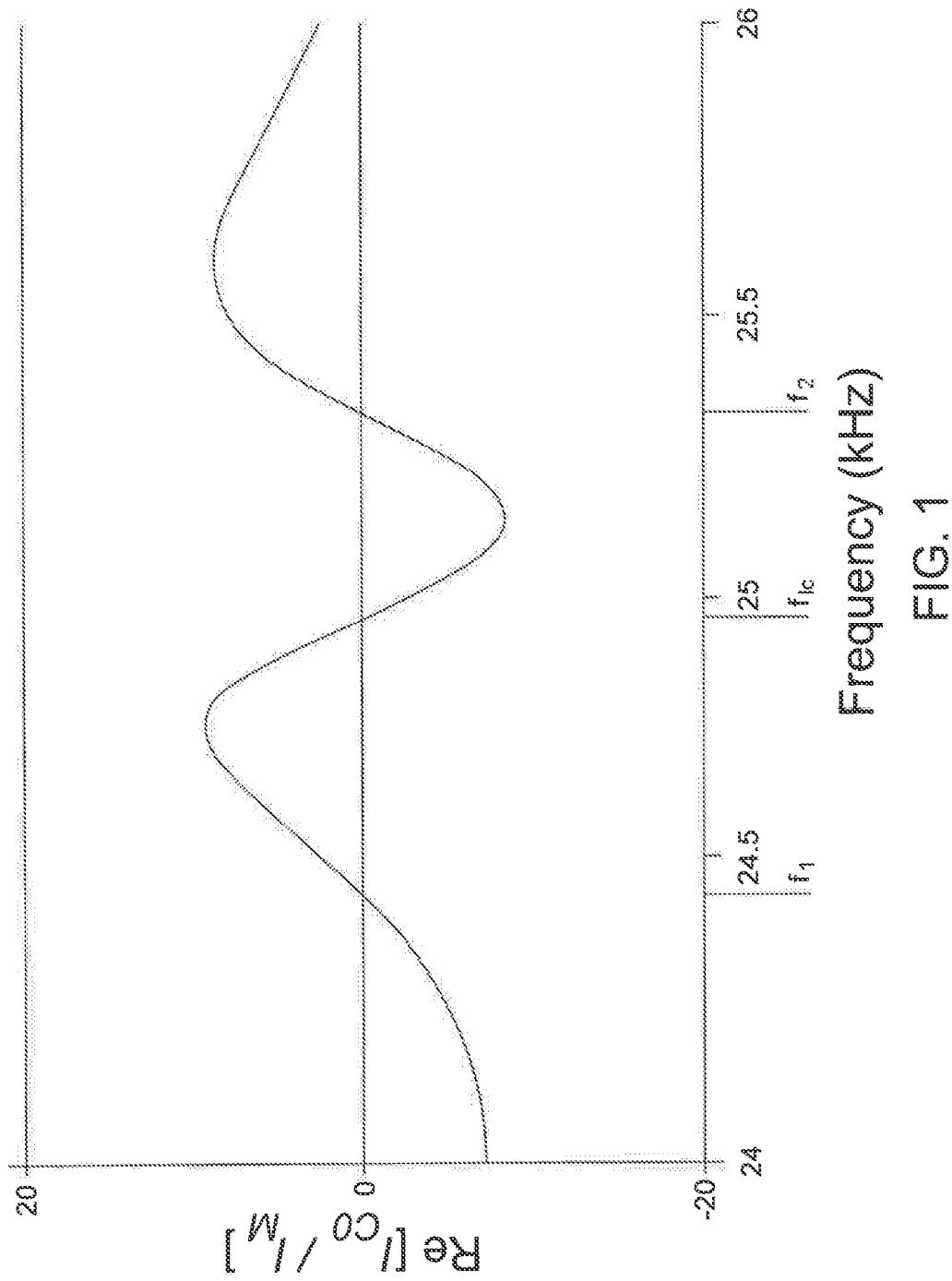
FIG. 1 is a graphical representation of the real component of the ratio between the current due to the capacitance of the handpiece drivers to the mechanical equivalent of current through the handpiece over frequency for a handpiece, including a handpiece of this invention.

Based on the these principles, system 30 of this invention is configured to apply a drive signal to the handpiece drivers 36 that is between the resonant frequencies associated with the first and second mechanical resonant modes of the handpiece. The particular frequency at which the drive signal is applied to the drivers is what is now referred to as the longitudinal mechanical cancellation frequency, $f_{LC}$. In the plot of FIG. 1, the longitudinal mode cancellation frequency $f_{LC}$ is 24.97 kHz.

Figure 10:
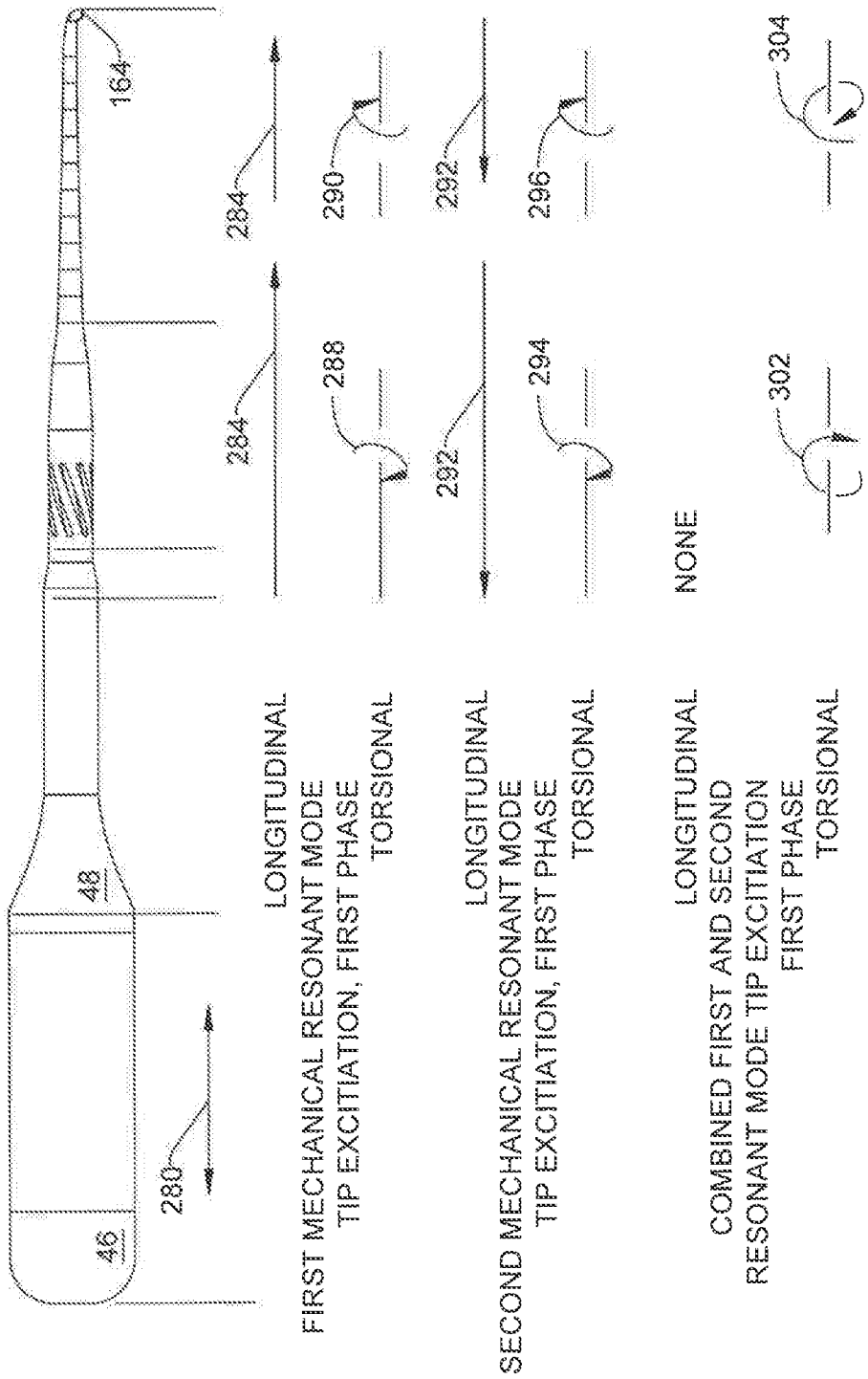
FIG. 10 is a diagrammatic representation of during a first phase of a vibratory cycle, the individual components of the longitudinal and mechanical vibrations of the handpiece and the sum of these components.
Figure 11:
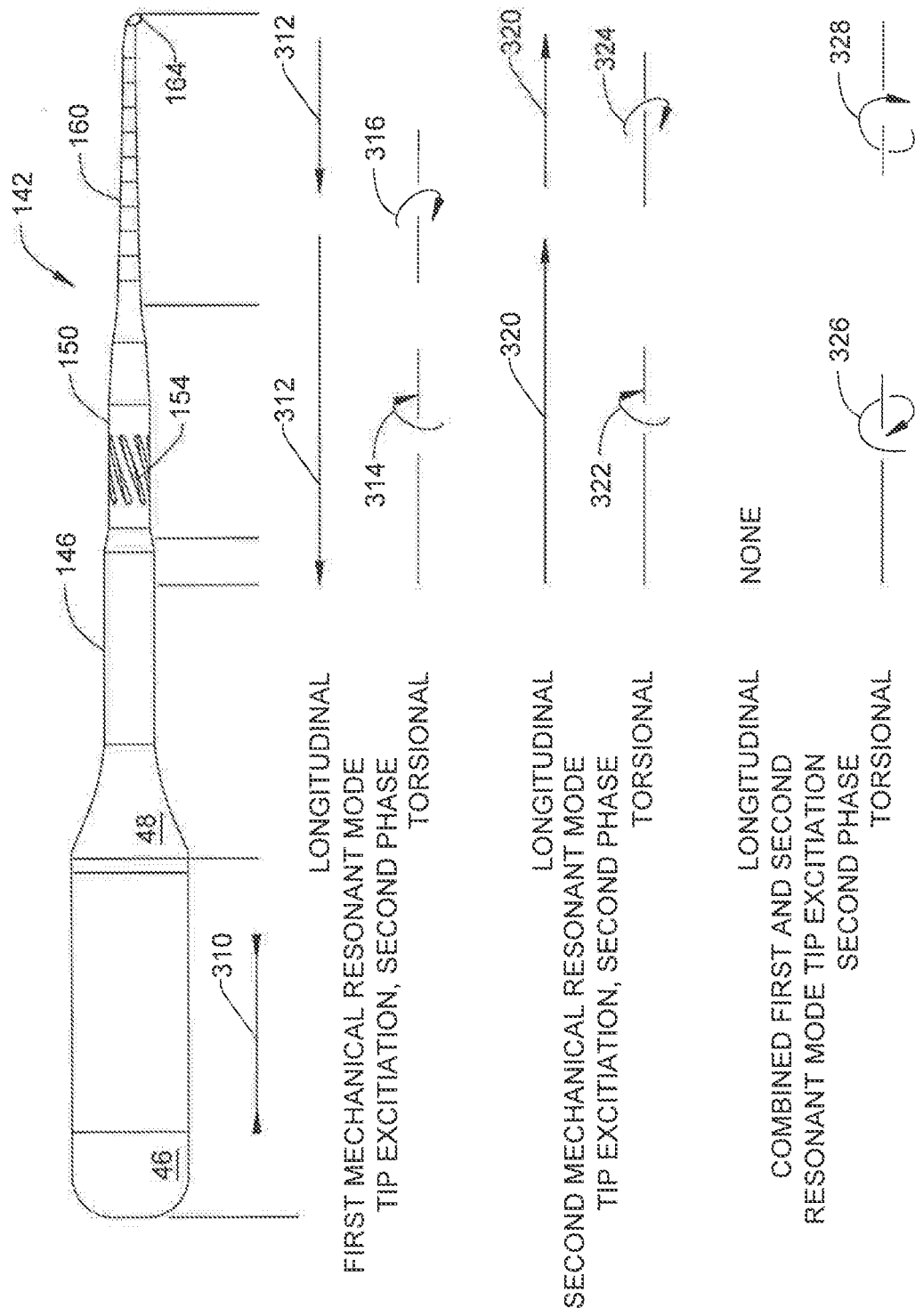
FIG. 11 is a diagrammatic representation of during a second phase of a vibratory cycle, the individual components of the longitudinal and mechanical vibrations and the sum of these vibrations.

When a drive signal is applied to the drivers 36 at the longitudinal mechanical cancellation frequency, the handpiece operates in what is referred to as the longitudinal mechanical cancellation mode. FIGS. 10 and 11 illustrate the components of the vibratory movements of the tip when the handpiece operates in this mode. FIG. 10 depicts what happens when the drivers apply a first force to the rest of the handpiece. Arbitrarily the drivers are outputting an expanding force represented by outwardly directed double head arrow 280. The drivers can be considered to apply this force to the other mechanical components of the tip during the first phase of a single vibratory cycle. For the purposes of this invention, the mechanical components of the handpiece are the vibrating components of the handpiece that apply mechanical energy to a mechanical load. These components include drivers 36, post 44, proximal end mass 46 horn 48 and tip 142. Sleeve 170 is typically not considered a component to which the equivalent of current flows. This is because, while the sleeve 170 vibrates, the vibration of the sleeve is due to the vibration of the other components. In other words, the sleeve 170 is part of the mechanical load to which the vibrations of the other mechanical components of the handpiece are applied. Accordingly, sleeve 170, for the purposes of analyzing the motion and signal flow of this invention, is not considered one of the mechanical components of the handpiece.

As a result of the drivers 36 applying an expanding force to the rest of the handpiece at the longitudinal mechanical frequency, the mechanical components of the handpiece are excited into undergoing their own longitudinal movement. Owing to the tendency of these components to vibrate at the first mechanical resonant mode, distal to the distal longitudinal node, this movement is a longitudinally expanding movement. This is represented by right directed arrows 284 of FIG. 10. While this movement is like the movement of the drivers is an expanding movement, this movement is out of phase with the vibrations of the drivers 36. Owing to the presence of the helical grooves 154, at the torsional boundary, a fraction of this longitudinal movement is converted into torsional movement of the tip 142. Adjacent the torsional boundary this movement is in the direction of curved arrow 288. Looking down the handpiece from the distal end, this movement would appear as a counterclockwise motion. At locations along the tip from the torsional node to the tip head, this movement would, from the same perspective appear as a clockwise rotation, the rotation represented by arrow 290.

The mechanical components of the handpiece also want to vibrate at the second mechanical resonant mode. Accordingly, the application of the same expanding force applied to mechanical components of the handpiece that causes out of phase longitudinal expanding vibrations of these components in the first mode, induces these same components, distal to the distal longitudinal node, into out of phase longitudinally contracting vibrations in the second mechanical resonant mode. These contracting vibrations are represented by left directed arrows 292. Owing to the presence of helical grooves 154 distal to the torsional boundary a fraction of these longitudinal vibrations are converted into torsional vibrations. Immediately adjacent the torsional boundary, these vibrations as represented by curved arrow 294, are in the counterclockwise direction. Distal to the torsional node, these vibrations, as represented by arrow 296 are in the clockwise direction.

Thus, when a drive signal at the longitudinal mechanical cancellation frequency is applied to the drivers 36, during one phase of the signal, the tendency of the handpiece mechanical components to expand distal to the longitudinal node is cancelled out by the tendency of these components to also want to contract. The tip head 164 therefore essentially does not engage in longitudinal movement.

Simultaneously in this phase, the opposed forces that would otherwise induce the longitudinal motion of the handpiece components are, as result of the presence of helical grooves 154, converted into torsional motion distal to the torsional boundary. These torsional motions are in phase with each other as represented by arrows. Since these torsional motions are in phase with each other, they are cumulative. In other words, during a phase of a vibration cycle the torsional movement of the tip head 164 is greater than the torsional movement of the tip head if the tip head was excited into a torsional movement owing the handpiece being driven to vibrate at a single one of the mechanical resonant frequencies. This is why, in FIG. 10, the curved arrow 302 that represents the sum of the torsional vibrations proximal to the torsional node is depicted as being longer than either one of arrows 288 and 294. For the same reason, curved arrow 304 that represents the sum of the torsional vibrations distal to the torsional node is depicted as longer than either one of arrows 290 and 296.

FIG. 11 depicts what happens when the drivers 36, during the second phase of a single vibratory cycle, apply a contracting force. As a result of the drivers contracting, post 44 pulls nut 46 and horn 48 towards each other is represented by inwardly directed double head arrow 310. As a result of the application of this force, and the tendency of these components to want to vibrate at the first mechanical resonant mode, distal to the distal longitudinal node this force appears as a longitudinally contracting movement. This movement is represented by the left directed arrows 312 of FIG. 11. This movement is out of phase with the contractions of the drivers 36. Owing to the presence of the helical grooves 154, at the torsional boundary, a fraction of this longitudinal movement is converted into torsional movement of the tip 142. Adjacent the torsional boundary this movement is in the clockwise direction of curved arrow 314. At locations along the tip from the torsional node to the tip head 164, this movement would, from the same perspective, appear as a counterclockwise rotation, the rotation represented by arrow 316.

The mechanical components of the handpiece also want to vibrate at the second mechanical resonant mode. Accordingly, the application of the same contracting force applied to mechanical components of the handpiece that causes out of phase longitudinal contracting vibrations of these components in the first mode, induces these same components, distal to the distal longitudinal node, into out of phase longitudinally expanding vibrations in the second mechanical resonant mode. These expanding vibrations are represented by right directed arrows 320. Owing to the presence of helical grooves 154 distal to the torsional boundary a fraction of these longitudinal vibrations are converted into torsional vibrations. Immediately adjacent the torsional boundary, these vibrations as represented by curved arrow 322, are in the clockwise direction. Distal to the torsional node, these vibrations, as represented by arrows 324 are in the counterclockwise direction.

So the sum of the vibratory movement of the handpiece in this second phase of a vibration cycle is the partial inverse of the vibratory movement in the first phase of the cycle. Again, the longitudinal vibrations, which are out of phase with each other, cancel each other out. This is why there is substantially minimal longitudinal movement of the tip. The torsional vibrations associated with the two mechanical resonant modes are in phase. This is why the tip 142 engages a torsional movement, a twist. As represented by the relative lengths of curved arrows 326 and 328 to curved arrows 314, 316, 322 and 324, this twist is greater in magnitude than the twist induced due to the tendency of the handpiece to want to vibrate either a single one of the mechanical resonant modes.

Consequently, when a drive signal at the longitudinal mechanical cancellation frequency is applied to the drivers 36, the handpiece mechanical components are driven to vibrate in a pattern, in which there is substantial torsional, twisting, vibration of the head with only minimal, if any, longitudinal movement of the shaft 144 and tip head 164.

Figure 12:
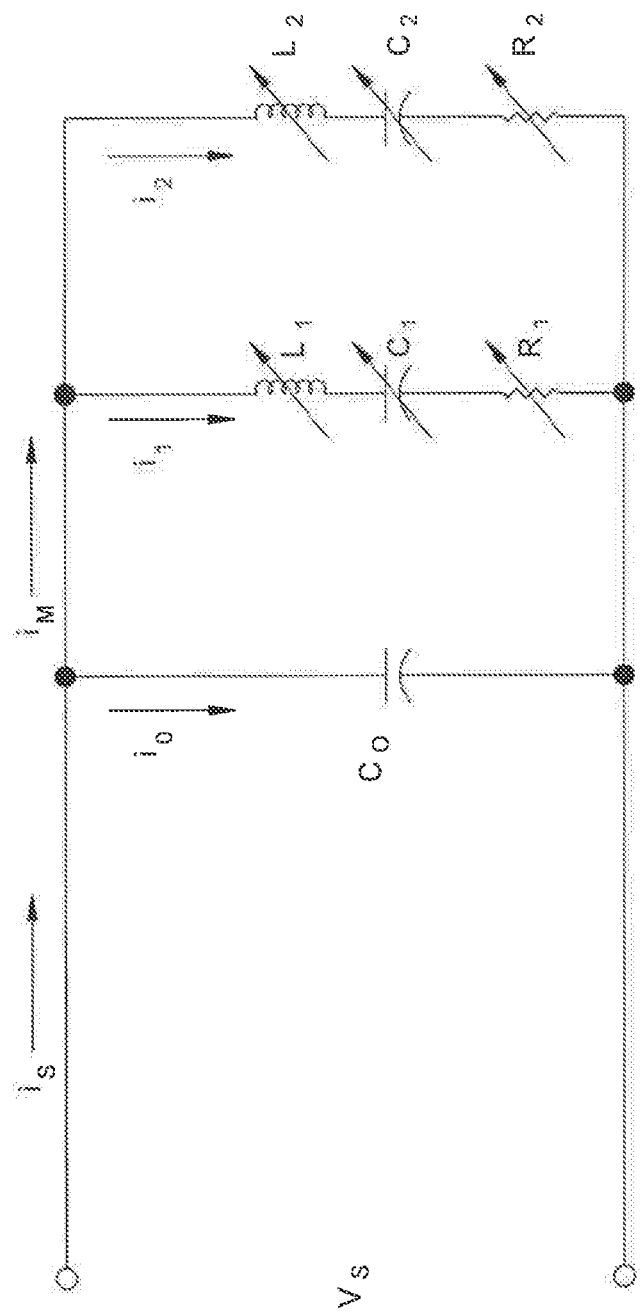
FIG. 12 is a schematic diagram of the impedances through which electrical current and mechanical equivalent are applied according to this invention.

An understanding of the characteristics of the drive signal applied to the drivers 36 so as to cause the handpiece to vibrate at the longitudinal mechanical cancellation frequency is obtained by initial reference to FIG. 12. This Figure represents the current flows through the components of the handpiece. The current of the drive signal, $i_S$, can be considered to be applied in parallel through three sets of components. The first set of components consists of the drivers 36 themselves. The impedance through these components, $Z_0$, is essentially the reactance of the drivers:

$$Z_0 = \frac{1}{j\omega C_0} \quad (2)$$

Driver capacitance is, for the purposes of this invention, constant. Therefore, the only variable that affects driver impedance is $\omega$, the frequency in radians of the drive signal.

The second set of components through which the drive signal current $i_S$ is applied are the mechanical components of the handpiece that cause the handpiece to vibrate at the first mechanical resonant mode. This current, it is understood, is not an actual electrical current. Instead, this current is a mechanical equivalent of current that flows through these components to induce the mechanical vibrations of these components. These components include drivers 36, post 44, proximal end mass 46 horn 48 and tip 142. Again, sleeve 170 is part of the mechanical load to which the vibrations of the other mechanical components of the handpiece are applied. Accordingly, it should be understood that sleeve 170 is not one of the components through which the mechanical equivalent of current flows.

In FIG. 12 this mechanical equivalent of current is $i_1$ since it is associated with the first mechanical resonant mode vibrations of the handpiece is more specifically the first resonant mode mechanical equivalent of current for the handpiece. The impedance $Z_1$ through which this mechanical equivalent is applied has: a resistive component due to the resistive characteristics, $R_1$, of the handpiece mechanical components when vibrating in the first mechanical resonant mode; an inductive reactance component due to the inductive characteristics, $L_1$, of the handpiece mechanical components when vibrating in the first mechanical resonant mode; and a capacitive reactance component, $C_1$, due to the capacitive characteristics of the handpiece mechanical components when vibrating in the first mechanical resonant mode. This impedance, $Z_1$, is therefore calculated based on the following equation:

$$Z_1 = R_1 + j\omega L_1 + 1/j\omega C_1 \quad (3)$$

As the load to which this handpiece mechanical components changes, the resistive, inductive and capacitive characteristics of these components change. This is why in FIG. 12, $R_1$, $L_1$, and $C_1$ are shown as variables.

The second set of components through which a portion of the drive current $i_S$ is applied are the mechanical components of the handpiece that cause the handpiece to vibrate at the second mechanical resonant mode. This portion of the current, current $i_2$, can be considered the second resonant mode mechanical equivalent of current through the handpiece. The impedance $Z_2$ through which the mechanical equivalent of current $i_2$ is applied has: a resistive component due to the resistive characteristics, $R_2$, of the handpiece mechanical components when vibrating in the second mechanical resonant mode; an inductive reactance component due to the inductive characteristics, $L_2$, of the handpiece mechanical components when vibrating in the second mechanical resonant mode; and a capacitive reactance component, $C_2$, due to the capacitive characteristics of the handpiece mechanical components when vibrating in the second mechanical resonant mode. This impedance is therefore calculated based on the following equation:

$$Z_2 = R_2 + j\omega L_2 + 1/j\omega C_2 \quad (4)$$

As mentioned above, changes in the load to which the mechanical components of the handpiece are applied result in changes in the resistive, inductive and capacitive characteristics of the handpiece. Accordingly, in FIG. 12, $R_2$, $L_2$, and $C_2$ are shown as variables.

Mathematically, and given Kirchhoff's Current Law, the above breakdown of the drive signal current $i_S$ can therefore be broken down as follows:

$$i_s + i_0 + i_1 + i_2 \quad (5A)$$

Rearranging Equation (5A) results in the following relationship:

$$i_1 + i_2 = i_s - i_0 \quad (5B)$$

This means that the mechanical equivalent of current through the mechanical components of the handpiece is equal to the difference between the current of the drive signal and the current flow through drivers 36. Given Equation (2), $$i_0 = jV_s 2\pi f C_0 \quad (6)$$

Here f is the angular frequency of the drive signal. Substituting Equation (6) into Equation (5B) yields the following result:

$$i_1 + i_2 = i_s - jV_s 2\pi f C_0 \quad (7)$$

The longitudinal mechanical cancellation frequency is above the resonant frequency of the first mechanical resonant mode. Therefore, when a drive signal at the longitudinal mechanical cancellation frequency is applied to the handpiece, impedance $Z_1$ is primarily inductive, due to $j\omega L_1$. The longitudinal mechanical cancellation frequency is below the resonant frequency of the second mechanical resonant mode. Therefore, when a drive signal at the longitudinal mechanical cancellation frequency is applied to the handpiece, impedance $Z_2$ is primarily capacitive due to $1/j\omega C_2$. This means that when a drive signal at the longitudinal mechanical cancellation frequency is applied to the drivers 36, impedance $Z_1$ is 180° out of phase with impedance $Z_2$. The reactive components of $Z_1$ and $Z_2$ therefore essentially cancel each other out. This means that when the drive signal at the longitudinal mechanical cancellation frequency is applied to the handpiece the parallel impedance of $Z_1$ and $Z_2$ is purely resistive.

At the longitudinal mechanical cancelation frequency, as at any frequency, impedance $Z_0$ of the drivers 36 is purely capacitive.

The above impedances being present when a drive signal at the longitudinal mechanical cancellation frequency is applied to the drivers means that when the handpiece is in this state that phase angle between current $i_0$ and mechanical equivalent of current $i_1+i_2$ is 90° out of phase.

Since both the electrical current and mechanical equivalent of currents through the handpiece have a magnitude and phase, these currents can be represented in polar form:

$$i_0 = A e^{j\Theta i_0} \qquad (8)$$

and $$i_1 + i_2 = B e^{j\Theta i_1 + ii_2} \qquad (9)$$

Dividing $i_0$ by $i_1+i_2$ when they are 90° out of phase therefore leads to the following:

$$\frac{i_0}{i_1 + i_2} = \frac{A e^{j\Theta i_0}}{B e^{j\Theta i_1 + ii_2}} = \frac{A e^{j\Theta i_0}}{B e^{j(\Theta i_0 - \pi/2)}} = \frac{A}{B} e^{j\pi/2} \qquad (10A)$$

Converting the right side of Equation (8A) to a rectangular number leads to the following:

$$\frac{i_0}{i_1 + i_2} = \frac{A}{B}\cos(\pi/2) + j\frac{A}{B}\sin(\pi/2) \qquad (10B)$$

$$= j\frac{A}{B} \qquad (10C)$$

The end result of Equation (10C) is based on the fact that, the cosine of 90° is zero and sine of 90° is one.

The above result means that, when the drive signal is at the longitudinal mechanical cancellation frequency, the real component of the ratio of electrical current flow through the drivers 36 and the mechanical equivalent of current through the mechanical components of the handpiece equals zero. Mathematically:

$$\mathrm{Re}\left\{\frac{i_0}{i_1 + i_2}\right\} = 0 \qquad (11A)$$

Substituting Equations (5) and (7) into Equation (11A) means that when the drive signal is at the longitudinal mechanical cancellation frequency, $$\mathrm{Re}\left\{\frac{jV_s 2\pi f C_0}{i_s - jV_s 2\pi f C_0}\right\} = 0 \qquad (11B)$$

The antecedent and consequent of Equation (11B) are identical to the antecedent and consequent of the prior art Equation (1). There are differences between applying a drive signal to the handpiece so as to cause the tip head 164 to undergo a simultaneous longitudinal vibrations and vibrations that are substantially torsional. When one wants to drive a handpiece to induce simultaneous torsional and longitudinal vibrations in the tip head 164, the target frequency is the resonant frequency associated with one of the mechanical resonant modes of the tip. Often this is the resonant frequency associated with the first mechanical resonant mode. In contrast, when applying a drive signal to the handpiece according to this invention the target frequency is the longitudinal mechanical cancellation frequency for the tip 142. This frequency is within the range of frequencies defined by the data in fields 196 and 198 of the tip memory.

A second difference between two systems is that the polarity of the ratio of the system of this invention is opposite the polarity of the ratio of Equation (1). The reason for this is that when regulating the drive signal so the handpiece is in a mechanical resonant mode, the slope of the relationship between the current applied to the drivers over the mechanical equivalent of current applied to the handpiece to frequency is positive. This means that by making the ratio of Equation (1) negative, should an evaluation of system state yield a negative result, the controller interprets the system as being in a state, in which in order to apply a drive signal to the handpiece that is at the resonant frequency of the resonant mode, it is necessary to increase the frequency of the drive signal. Conversely, should the evaluation of Equation (1) yield a positive number, the controller interprets the system as being in a state, in which in order to apply a drive signal to the handpiece that is at the resonant frequency of the resonant mode, it is necessary to decrease the frequency of the drive signal.

In contrast, when regulating a system according to this invention, to apply a drive signal at the longitudinal mechanical cancellation frequency to the handpiece, the slope of the relationship between the current applied to the drivers over the mechanical equivalent of current applied to the handpiece to frequency is negative. As discussed above the ratio of Equation (11B) is of opposite polarity to the ratio of Equation (1). This means that should an evaluation of system state of this invention yield a positive result, processor 266 interprets the system 30 as being in a state, in which, to apply a drive signal at the longitudinal mechanical cancellation frequency to the handpiece that is at the resonant frequency of the resonant mode, it is necessary to increase the frequency of the drive signal. Conversely, should the evaluation of Equation (11B) yield a negative number, processor 266 interprets the system as being in a state, in which in order to apply a drive signal to the handpiece that is at the longitudinal mechanical cancellation frequency, it is necessary to decrease the frequency of the drive signal.

From the above it should also be appreciated that the total mechanical equivalent of current through the mechanical components of the handpiece is equal to the sum of the mechanical equivalents of current through the handpiece. Mathematically, $$i_M = i_1 + i_2 \qquad (12)$$

III. Actual Operation

Operation of system 30 of this invention starts with the coupling of the tip 142 to the handpiece 32. Sleeve 170 is fitted over the tip and also attached to the handpiece. 32. Cable 228 is attached to the control console 230. Console 230 is then ready to be turned on. The above sub-steps form the initial assembly and activation of the system, step 332 in FIG. 13A. When the control console 230 is initially turned on, processor 266 reads the data stored in handpiece memory 56 and tip memory 184, step 334. The processor 266 receives these data by asserting the appropriate commands to the memory reader 262.

Based on the read data, in a step 336, processor completes the initial configuration of the system. Step 336 includes the performance of a number of evaluations to determine whether or not the system 30 is properly configured for use. These evaluations include: determining if the handpiece is one to which the control console 230 can supply a drive signal; and determining if tip 142 is one that is appropriate for actuation by the handpiece. These evaluations may be based on data from the handpiece identification field 62 and from the tip identification field 188. Processor 266 also evaluates whether or not the handpiece 32 and tip 142 are in conditions for use based on the read data from the handpiece use history field 78 and the tip use history field 218. An example of data indicating that use may be inappropriate are data indicating that a particular component, the handpiece or tip, has been used for a number of times or an overall time that exceeds the designed life cycle for the component.

Based on the data in the handpiece memory 56, the tip memory 184 and the practitioner commands, the processor in a step 338 established a selected maximum equivalent of current $i_M^{SELECTMAX}$ that is be flowed through the mechanical components of the handpiece. Current $i_M^{SELECTMAX}$ is understood to be no greater than the maximum mechanical equivalent of current $i_M^{MAX}$ as read from the tip memory 184.

Step 340 represents processor 266 waiting to determine if the control member has been actuated to indicate that the tip 142 is to be vibrated. In the described embodiment of the invention, processor 266 executes step 340 by monitoring the signal output by footswitch 270. When the practitioner wants to actuate the tip 142, he/she depresses the footswitch 270. The magnitude of tip head vibrations is set by the practitioner controlling the extent to which the footswitch 270 is depressed.

In response to the practitioner depressing the control member, the processor in a step 342 calculates a target current $i_M^{TARGET}$, sometimes referred to as the target mechanical equivalent of current. Target current $i_M^{TARGET}$ is the mechanical current that the processor determines should be applied to the mechanical components of the handpiece 32. Target current $i_M^{TARGET}$ is based on current $i_M^{MAX}$ retrieved from the handpiece memory and the extent to which that footswitch 270 is depressed. The target current can be calculated using a first order equation:

$$i_M^{TARGET} = D i_M^{SELECTMAX} \tag{13}$$

Coefficient D is between 0.0 and 1.0, inclusive. If, for example, the practitioner depresses the footswitch 270 to have the handpiece tip 164 undergo the vibrations of maximum amplitude, processor 266 sets coefficient D to unity. If the setting of footswitch 270 indicates that the vibrations are to be at an amplitude less than the maximum, processor 266 sets coefficient D to a value less than one.

In step 344, processor 266 then generates the initial WAVEFORM_SET signal. The potential of this signal is set to cause the power supply to output a drive signal that is appreciably less than the maximum drive signal voltage $V_S^{MAX}$ retrieved from the handpiece memory 58. For example, in some versions of the invention the potential of the WAVEFORM_SET signal is set cause the outputting a drive signal with a potential is between 0.02 and 0.10 of voltage $V_S^{MAX}$. More particularly, the WAVEFORM_SET signal is set to cause the voltage of the drive signal to a potential that is between 0.03 and 0.07 of voltage $V_S^{MAX}$. The relationship between the voltage of the WAVEFORM_SET signal and drive signal voltage $V_S$ of the drive signal is typically a first order relationship. The determination of the voltage of the WAVEFORM_SET signal as a function of the target drive signal voltage is based on potential of the target drive signal voltage and a coefficient and offset values previously stored in the processor 96.

As part of step 344, processor 266 also establishes the frequency of the WAVEFORM_SET signal. When the control member is initially depressed to actuation the handpiece, processor 266 sets the frequency of the WAVEFORM_SET signal to be between the minimum possible longitudinal mechanical cancellation frequency, the frequency from field 196 in the tip memory 184, and the maximum possible mechanical cancellation frequency, the frequency from filed 198 in the tip memory. While not specifically called out, in step 342 processor 344 asserts any necessary enable signals to the power supply 232, amplifier 234 and any safety components internal to the console 230. The assertion of these signals ensures that the power supply 232 outputs the necessary rail signal to the amplifier, the amplifier 234 applies the intended signals across the transformer primary winding 244. The drive signal is induced to develop across the secondary winding 248.

As a result of the signal flow across transformer 238, the drive signal is applied to handpiece 32. This results in the cyclic expansion/contractions of the drivers 36. Since the drivers vibrate a frequency between the first and second mechanical resonant modes of the handpiece, the handpiece itself engages in the simultaneous out of phase vibrations at both these resonant modes. This results in the portion of the tip distal to the torsional boundary engages in a vibrations that are substantially torsional and only if nominally if at all longitudinal.

System 30 then engages in a feedback control process to ensure that the output drive signal induces vibrations of appropriate amplitude and direction in tip head 164. To perform this control, in step 346, console 230 monitors the voltage $V_S$ of the drive signal across the handpiece. Specifically, in step 346 the signal representative of the drive signal voltage $V_S$ output by the voltage measuring circuit 252 is applied to processor 266. Also in step 346, the console 230 monitors current $i_S$, the current of the drive signal sourced to the handpiece 32. This portion of step 346 is the application of the output signal produced by current measuring circuit 256 to the processor 266

In a step 348, processor 96 determines the total mechanical equivalent of current $i_M$ applied to the This calculation is based on a combination of Equations (7) and (12). Processor 266 is able to make this determination since it has data defining the four variables upon which this determination is based: current $i_S$ from the current measuring circuit 256; frequency ω based on the fact that processor sets the frequency of the drive signal; voltage $V_S$ from the voltage measuring circuit 252; and driver capacitance $C_o$. While driver capacitance $C_o$ is a variable, in Equation (7) it is fixed and known variable read from the handpiece memory 56.

In a step 350 the total mechanical equivalent of current $i_M$ is compared to current $i_M^{TARGET}$. More particularly, this comparison is made to determine if the actual current flow through the mechanical components of the handpiece is equal to or substantially the same as the target flow. Here, substantially the same is considered to be the state when the currents are within 20 or less mAmps of each other and more often 10 or less mAmps from each other, preferably 2 mAmps or less and, more preferably, 1 mAmp or smaller. Alternatively, the currents can be considered substantially the same if they are within 10% or less of each other, more preferably within 5% or less of each and ideally, within 1% or less of each other.

If the currents are substantially equal, system 30 is in the state in which the equivalent of current applied to the mechanical components of the handpiece is at level at which the application of the drive signal, assumed to be at the correct frequency, is inducing vibrations of appropriate amplitude in tip head 52. If system 30 is in this state, processor 96 proceeds to step 164.

In many situations, the comparison of step 350 indicates that the total mechanical equivalent of current $i_M$ is not substantially equal to target current $i_M^{TARGET}$. When system 30 is in this state, processor 96 in a step 352 resets the voltage of the WAVEFORM_SET signal. More specifically, the processor 96 calculates a value for drive signal voltage $V_S$ that would, based on Equation (7), result in an adjusted current flow through the mechanical components of the handpiece that substantially equal to target current $i_M^{TARGET}$. This calculation of step 352 is executed based on driver capacitance and drive signal frequency remaining constant.

Not identified is the step of where, as a result of the resetting of the voltage of the WAVEFORM_SET signal, amplifier resets the potential of the signal applied across the transformer primary winding 244. This results in a change in the drive signal voltage $V_S$ that appears across the transformer secondary winding 248.

In a step 356 the processor determines if the frequency of the drive signal is at or substantially equal to the longitudinal mechanical cancellation frequency of the handpiece. This determination is made by evaluating whether or not the ratio of Equation (11B) is equal to or substantially equal to zero. Here, substantially equal to zero means the real components of the ratio is 0.10 or less, preferably 0.05 or less and more ideally 0.01 or less.

The comparison of step 356 may indicate that the drive signal applied to the handpiece is at or substantially equal to the longitudinal mechanical cancellation frequency of the handpiece. This is the target state for the drive signal. This means that the drive signal is inducing expansions/contractions of the drivers 36 that result in the sections of the tip distal to the torsional boundary engaging in substantial torsional vibrations and minimal, if any, longitudinal vibrations.

It may be determined in the evaluation of step 356 that the drive signal is not being applied to the handpiece at or near the longitudinal mechanical cancellation frequency. If processor 266 makes this determination, in a step 358 the processor resets the frequency of the WAVEFORM_SET signal, step 358. If the result of the evaluation of step 356 is negative, the processor 266 considers the system to be in a state in which owing to the ratio on the left side of Equation (11B) being negative, in step 358 processor 266 interprets the system 30 as being in state in which the frequency of the drive signal should be decreased. If the calculation of step 356 yields a positive result, processor 96 considers the system 30 is in a state in which it is necessary to increase the frequency of the drive signal to ensure that the drive signal frequency is closer to the longitudinal mechanical cancellation frequency of the handpiece.

In step 358, processor assumes the current $i_S$, voltage $V_S$ and driver capacitance $C_O$ are constant. In the iterative process, different frequencies are injected into Equation (11B). As a result of the new execution of Equation (11B) it may be determined that the real components of the ratio of the current flow through the drives and the equivalent of current applied to the mechanical components of the handpiece is less (or substantially less) than zero. If this condition exists, then, in the next iteration the injected frequency will be less than the previously injected frequency. As a result of the execution and evaluation of Equation (11B) it may be determined that the ratio is greater (or substantially greater) than zero. If this condition exists, then, in the next iteration the injected frequency will be greater than the previously injected frequency. If the end result of the calculation is that the ratio is zero or substantially zero, then the frequency of the drive signal is set to the injected frequency. Processor 266 then adjusts the frequency of the WAVEFORM_SET signal output to amplifier 234 based on the results of these calculations. Control console 230 then, in turn, outputs a drive signal to the handpiece that is at the longitudinal mechanical cancellation frequency of the handpiece 32.

While not shown, it is understood that characteristics of the drive signal applied to the handpiece 32 are limited by the boundary parameters read from the handpiece. Specifically, the adjusting of the WAVEFORM_SET signal is limited to ensure that the drive signal does not exceed the potential specified by the maximum voltage level $V_S^{MAX}$. Adjustment of the WAVFORM_SET signal is further limited to ensure the current of drive signal applied to the handpiece does not exceed $i_S^{MAX}$ and that the mechanical component of current does not exceed $i_M^{MAX}$.

It should also be understood that the adjustment of voltage and frequency of the WAVEFORM_SET signal that occurs in steps 352 and 358 are based on the PID coefficients read from the handpiece memory 56 and tip memory 184. Typically, the coefficients in the tip memory 184 are coefficients upon which these characteristics of the WAVEFORM_SET signal are adjusted.

Figure 13A:
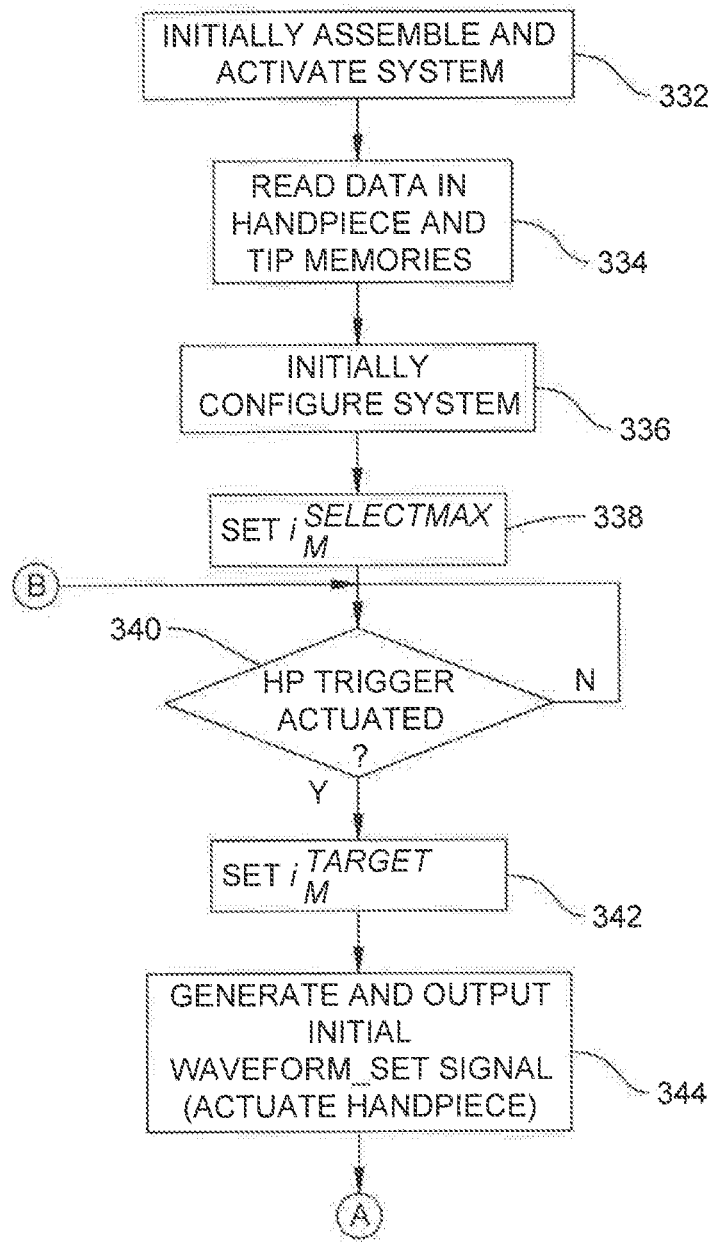
FIGS. 13A and 13B, when assembled together, form a flow chart of the operation of the system of this invention.
Figure 13B:
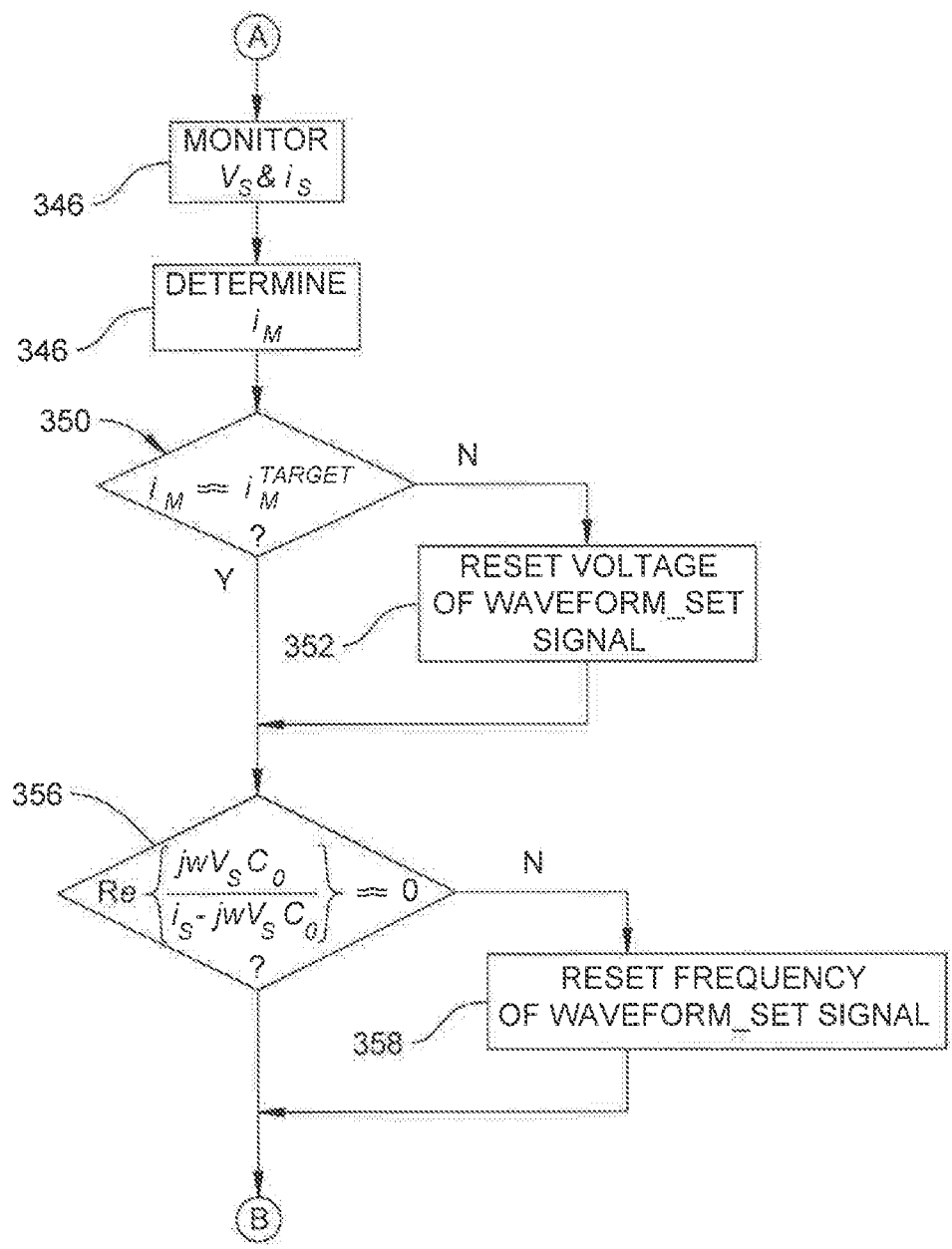

In FIGS. 13A and 13B, after the execution of step 356 or, if necessary, step 358, the system is shown looping back to step 340. This is because the processes of recalculating target current $i_M^{TARGET}$ and selectively adjusting the potential and frequency of the drive signal are generally performed as long as the system remains actuated.

There are a number of reasons why the control loop is repetitively executed. Generally, it should be understood that, if as a result of the adjustment of the frequency of the drive signal is adjusted, there will be a change in the impedance of both driver impedance $Z_0$ and impedance $Z_1$ and $Z_2$ of the mechanical components of the handpiece. This results in a change of the current flow through the handpiece and, more particularly, the total mechanical equivalent of current $i_M$ through the mechanical components of the handpiece. System 30 detects these changes as changes in the measured values $V_S$ and $i_S$. Thus after step 356 or 358 is executed, the next evaluation of step 350 will most likely indicate that the system is in a state in which the total mechanical equivalent of current $i_M$ has shifted from the target current $i_M^{TARGET}$. This will necessitate a new execution of step 352 to adjust the magnitude of the voltage of the drive signal.

Similarly, the adjustment of the potential of the drive signal will also result in changes of voltage $V_S$ and current $i_S$. This means that the next time step 164 is executed the evaluation will indicate that the drive signal is no longer at the longitudinal mode cancelation frequency of the mechanical components of the handpiece.

After plural cyclings through the control loop, the console 266 asserts a drive signal that results in the current flow through the mechanical components of the handpiece that is substantially equal to $i_M^{TARGET}$ and is at the longitudinal mode cancelation frequency of the handpiece mechanical components. At start up, assuming the tip head is not applied against tissue, it is believed that the system reaches this state in 2 seconds or less and, more often 1 second or less.

A further reason the control loop is continuously executed has to do with the very nature of how handpiece 32 is employed. For the handpiece to function, the head 164 is placed against tissue, (step not shown). This is because it is the back and forth movement of the teeth against the tissue that result in the sawing, ablation, emulsification, collectively the removal of, the tissue. Again, in some implementations of the invention, this back and forth movement is what results in the cavitation of the fluid adjacent the tissue and, in some instances the tissue itself.

When the head 164 is placed against tissue, a mechanical load is placed on the components forming the handpiece. This mechanical load changes the impedance of the mechanical components of the handpiece. Here, the impedance is understood to be the impedances associated with both the first and second mechanical resonant modes of the handpiece. Also, when system 30 is actuated, the temperature of the mechanical components of the handpiece often change. This change in component temperature results in a change in the impedances of these components. The change in component properties can cause a shift in longitudinal mechanical cancellation frequency of the handpiece.

The resultant change in impedance and longitudinal mechanical cancel frequency results in changes in the flow of both current $i_S$ through the handpiece and the total mechanical equivalent of current $i_M$. The continual execution of the control loop thus ensures that when these changes in impedance occur, the drive signal is reset to ensure that the mechanical equivalents of current is substantially equal to the target current $i_M^{TARGET}$ and the frequency of the drive signal is substantially equal to longitudinal mechanical cancelation frequency of the mechanical components of the handpiece. The maintaining of the characteristics of the drive signal close to these target parameters ensures that as the mechanical load to which the tip head 52 is exposed changes, the amplitude of the vibrations of the head remain substantially constant and the tip head 164 and adjacent distal section 160 of the shaft 144 do not engage is substantial longitudinal movement.

Further, during the time period in which the handpiece 32 is actuated, the practitioner may want to adjust the amplitude of tip head vibrations. This adjustment occurs by the resetting of control member 270. (Adjustment not illustrated.) Once this adjustment occurs, in the subsequent executions of step 148 the newly calculated target current $i_M^{TARGET}$ will be different than the previously calculated target current. This in turn will most likely mean that as a result of the next execution of step 350 it will be determined that the mechanical equivalents of current, $i_1+i_2$, is no longer substantially equal to the target current $i_M^{TARGET}$. For the reasons set forth above, this will most likely result in an adjusting of the potential and frequency of the drive signal.

Accordingly, the above described control loop starting with the evaluation of step 340 is continuously executed as long the foot pedal 270 or other on/off control remains actuated. The practitioner deactivates the handpiece by releasing the foot pedal 270. This results in the processor, in one of the subsequent executions of step 340, receiving a signal that this control member is in the off position. In response to processor 266 receiving this signal, the processor negates the application of the signals that were being asserted so as to cause the outputting of the drive signal, (step not shown). System 30 returns to the wait state, the continuous monitoring of the signal from the on/off control member to determine if the practitioner wants to actuate the handpiece 32.

It should be appreciated that after the handpiece is actuated there will eventually become a time in which it is no longer necessary to apply the vibrating tip head 164 to the tissue. The practitioner stops depressing the control member, footswitch 270. The processor 266 detects the occurrence of this event in the following execution of step 340. When this event occurs, the processor negates the application of the WAVEFORM_SRT signal, step not shown. This results in the control console ceasing to apply the drive signal to the handpiece drivers 36. This results in the termination of the vibration of the tip 142. Processor 266 continues to repeatedly execute step 340 to determine if, the practitioner again wanting to vibrate the tip, the control member 270 is again actuated.

System 30 of this invention is constructed so that, owing to the repetitive execution of steps 356 and 358, the system maintains the drive signal at a frequency that is substantially equal to the longitudinal mechanical cancellation frequency of the handpiece 32. This relationship is maintained when the resonant frequency of the handpiece mechanical components changes due to the mechanical loading and/or temperature change of these components System 30 invention is able to vibrate the head of the tip at the desired amplitude even when the tip and the other components of the handpiece are subjected to mechanical loading or undergo temperature changes. This reduces the need for the surgical personnel using the system having to continuously adjust the drive signal to ensure that the tip head continuously vibrates at the desired amplitude.

Also, during the course of a procedure the tip head may be suddenly pressed against tissue. This causes a rapid significant increase in the impedance of the mechanical components of the handpiece. In response to this rapid change in impedance, system 30 of this invention rapidly adjusts the potential and frequency of the drive signal. The adjustment of these characteristics of the drive signal serve to ensure that the tip head vibrations maintain the desired amplitude. This reduces the extent to which the sudden mechanical loading of the handpiece results in a like sudden reduction in the amplitude of the tip head vibrations.

By applying a drive signal at the longitudinal mechanical cancellation frequency to the handpiece, system 30 of this invention induces vibrations in the tip 142 that are substantially torsional. The tip shaft 144 engages in minimal, if any longitudinal vibrational movement. During the course of a procedure the shaft 144 may be pressed against tissue adjacent the tissue against which the tip head 164 is applied in order facilitate the placement of the tip head. Since the shaft 144 engages in only minimal longitudinal movement, the likelihood that this movement could induce cavitation that would result in the unwanted removal of the tissue against which the shaft is pressed is likewise substantially, if not totally, eliminated.

It likewise should be appreciated that this system does not require processor 266 to match the characteristics of the handpiece 32 and tip 142 to the capacitance, resistance or inductance of a component internal to the control console 230. A single console 230 can therefore be used to construct a system 30 of this invention with different handpieces 32 and tips 142, each with their own impedance characteristics. The console, based on the data read from the handpiece memory 56 and tip memory 184 configures the system 30 for each handpiece and tip assembly. Likewise, a handpiece and a tip can be used with different control consoles to assembly the system 30 of this invention.

It should similarly be appreciated that in the above described version of the invention, plural different tips 142, each tip having its own longitudinal mechanical cancellation frequency, can be attached to and subsequently driven by a single handpiece 32. One benefit of this feature of this invention is that plural different types of tips, each with own physical structure and therefore longitudinal mechanical cancellation frequency can be attached to a common handpiece. A second benefit of this feature is that it makes possible to, post manufacture, evaluate each tip to determine the longitudinal mechanical cancellation frequency for that tip. This means that the data for each tip used to supply the drive signal for that tip accounts for manufacturing variations between individual tips. Again, both types of tips that are different to either basic design or manufacturing variations, can be driven by a single handpiece. This facilitates providing a system of this invention that does not require the expense of providing a handpiece that is specifically associated for use with the associated tip 142.

System 30 of this invention is further designed to apply a mechanical equivalent of current to the mechanical components of the handpiece that is substantially equal to the target current. This target current is based on the practitioner's setting of the desired amplitude of tip head vibrations. Thus, the system of this invention provides the practitioner with a relatively accurate means of controlling the amplitude of the tip head vibrations.

IV. Alternative Embodiments

The above is directed to one specific version of this invention. Alternative versions of the invention may have features that are different from what has been described.

For example, the components used to construct this invention may be different from what has been described. In some versions of the invention, the handpiece 32 and tip 142 may be a single piece unit.

The features integral with the tip that convert the longitudinal vibratory motion into torsional vibratory motion may not always be helical grooves. In some versions of the invention, these features may be grooves but they may not be helical. An example of an alternative groove structure are diagonal grooves. The difference between these two grooves is that a helical groove has a longitudinal axis that, extending proximal to distally along the tip, curves around the longitudinal axis of the tip. A diagonal groove has a longitudinal axis that is linear in shape.

The stated frequencies, voltages, currents, capacitances and other quantified values, unless present in the claims are understood be only examples and do not limit the scope of the invention.

The control console 230 may include other components that generate the drive signal that varies both in potential and frequency. Depending on the construction of these components, the console may not include a transformer across which an input signal is applied in order to produce the drive signal. Similarly, in some versions of the invention, resistor circuits as opposed to inductors may be incorporated into the console in order to provide signal representative of one or both of the drive signal voltage $V_S$ and the drive signal current $i_S$.

Likewise in some versions of the invention, the console may include a first circuit that sets the frequency of the drive signal and a second circuit, a variable gain amplifier that sets the potential of the drive signal. In these versions of the invention, the processor 266

The type of memory device that contains the data describing the characteristics of the handpiece and tip that are needed to regulate the outputting of the drive signal may vary from what has been described. For example, one or more of these memories may be a EEPROM, a bar code or some other machine readable device. In some versions of the invention, one or more of the handpiece and tip may not even have a memory. In these versions of the invention, personnel are required to manually enter the handpiece and tip characteristics into the console in order to ensure the system 30 is properly configured.

The sequence of steps by which the console 230 sets the potential and frequency of the drive signal may likewise vary from what has been described. For example, in an alternative configuration of the system, the console may first set the frequency of the drive signal before setting the voltage of this signal. Again, depending on the construction of the invention, the console may not set the frequency and voltage of drive signal by setting the corresponding characteristics of a single WAVEFORM_SET signal. In some versions of the invention, in order to regulate the operation of the components that actual generate the drive signal, the processing circuit may generate two control signals. A first one of the control signals is used to set the voltage of the drive signal. The second control signal is used to set the frequency of the drive signal.

In the described version of the invention, console 230 is configured to initially set the drive signal to a frequency that is the lowest possible longitudinal mechanical cancellation frequency for the tip. Other versions of the invention may be configured to employ an alternative frequency as the initial frequency of the drive signal. For example, in some version of the invention, the initial frequency of the drive signal may be the highest possible longitudinal mechanical cancellation frequency. Alternatively the drive signal may be set a frequency that is between the lowest and highest longitudinal mechanical cancellation frequencies for the tip. In some versions of the invention, the memory integral with the tip may include data that defines the initial frequency setting of the longitudinal drive signal.

In the above description, driver capacitance $C_O$ is assumed to be constant. This is for the purposes of understanding this invention. In actuality, driver capacitance may drift over time. This drift can be due to effects such as aging of the drivers or, during a single procedure, a change in temperature of the drivers. Therefore, some control consoles integrated into the system of this invention, include a means to determine driver capacitance. The exact means of making this determination is not part of the invention. From time to time during a procedure, this means of determining driver capacitance is used to provide an updated measure of driver capacitance $C_O$ for use in the evaluations of used to determine the mechanical equivalent of current.

Further the system of this invention may be configured to, based on the preferences of the practitioner and the specifics of the procedure being performed apply a drive signal to the handpiece that causes the tip to vibrate in one of three states. By entering first set of commands into the console the system would source drive signals to cause the tip to vibrate as described above, substantially torsionally with minimal, if any, longitudinal vibrations.

By entering a second set of alternative commands into the console 230, the system sources drive signals that cause the tip to vibrate at one of the mechanical resonant modes. For the system to operate in this mode, the frequency of the drive signal is set based on the data in fields 194 and 195 of the tip memory 184 that define the range of frequencies for the drive signal when the tip is to be vibrated in the mechanical resonant mode. When the console is so set it would operate as described in the incorporated by reference PCT Pub. No. WO 2015/021216 A1. When the system operates in this mode it would be appreciated that distal to the torsional boundary, the tip shaft 14 and tip head 164 would engage in simultaneous longitudinal and torsional movement. A practitioner may want the handpiece to operate in this mode if it is believed that the combined longitudinal and torsional movement of the tip head 164 would result in the optimum removal to tissue and the effects of the longitudinal motion of the shaft 144 are tolerable.

By entering a third set of commands into the console 230, the system sources drive signal across the drivers 36 that is a combination of the drive signals needed to drive the tip at the first resonant mode and the drive signals needed to drive the tip at the second resonant mode. When the console is so set, the system operates as described in the incorporated by reference PCT App. No. PCT/US2015/044023. A practitioner may want the handpiece to operate in this mode in a situation in which it is desirable have the tip head 164 engage in non-linear motion in order to remove tissue and the effects of the longitudinal motion of the tip head are tolerable.

For system 30 to be able to operate in the third mode, the tip memory would essentially contain two versions of field 194 and two versions of field 195. In the first versions of field 194 and field 195 data are stored that define the range of resonant frequencies of the first mechanical resonant mode. The second versions of field 194 and 195 data are stored that define the range of resonant frequencies associated with the second mechanical resonant mode.

Similarly, by entering a fourth set of commands into the console, the system can be set to source a drive signal that is at a frequency between the resonant frequency of one of the mechanical resonant modes and the longitudinal mechanical cancelation frequency. Thus, when the system is operated in this state, there is a partial cancelation of the longitudinal motion of the tip head 164 and the adjacent distal section 160 of the shaft. This mode of operation may be desirable if, for a given procedure, it is be appropriate to excite the tip head 164 into vibrations that cause the tip to engage primarily in torsional movement with some but not the full longitudinal movement.

Additional data that may be stored in the tip memory include data defining the range of mechanical equivalents of current for each of the resonant modes.

Accordingly, it is the object of the appended claims to cover all such variations and modifications that come within the true spirit and scope of the invention.

What is claimed is:

1. A method of vibrating an ultrasonic surgical tip, said method including the steps of:
    providing a handpiece having at least one driver that, in response to the application of an AC drive signal, cyclically expands and contracts and a tip that is connected to the at least one driver, the tip having opposed proximal and distal ends, the proximal end being connected to the at least one driver so as to vibrate longitudinally in response to the expansions and contractions of the at least one driver, a feature between the proximal and distal ends that converts longitudinal vibrations induced in the proximal end of the tip into vibrations that, adjacent the distal end of the tip, have a longitudinal component and a torsional component and a head at the distal end configured to perform a procedure;
    sourcing the AC drive signal from a power supply to the handpiece that varies both in frequency and potential;
    determining a target mechanical equivalent of current through mechanical components of the handpiece;
    measuring a current sourced to the handpiece and a voltage across the output of the power supply;
    based on the current sourced to the handpiece, the voltage across the power supply, the frequency of the AC drive signal and a capacitance of the at least one driver, calculating a mechanical equivalent of current through mechanical components of the handpiece;
    comparing the target mechanical equivalent of current to the calculated mechanical equivalent of current;
    based on said comparison of the target mechanical equivalent of current to the calculated mechanical equivalent of current, selectively setting the potential of the AC drive signal sourced by the power supply;
    based on the current sourced to the handpiece, the voltage across the power supply, the frequency of the AC drive signal and the capacitance of the at least one driver, calculating a ratio between current through the at least one driver to the calculated mechanical equivalent of current through the mechanical components of the handpiece; and
    based on the ratio between the current through the at least one driver to the calculated mechanical equivalent of current through the mechanical components of the handpiece, setting the frequency of the AC drive signal sourced by the power supply to a frequency between resonant frequencies of two adjacent mechanical resonant modes of the handpiece so that a longitudinal component of the vibrations at the tip head of a first one of the mechanical resonant modes at least partially cancels out a longitudinal component of the vibrations of the tip head of a second one of the mechanical resonant modes.

2. The method of claim 1, wherein said step of sourcing the AC drive signal from a power supply to the at least one driver prior to said step of setting the frequency of the AC drive signal based on the ratio comprises initially setting the frequency of the AC drive signal to a frequency between the resonant frequencies of the two adjacent mechanical resonant modes of the handpiece so the longitudinal component of the vibrations of the tip head of the first one of the mechanical resonant modes at least partially cancels out the longitudinal component of the vibrations of the second one of the mechanical resonant modes.

3. The method of claim 1, wherein said step of calculating the mechanical equivalent of current through the mechanical components of the handpiece comprises determining the difference between the current sourced to the handpiece and the current through the at least one driver.

4. The method of claim 3, further comprising calculating the current through the at least one driver as a function of the capacitance of the at least one driver and the voltage and the frequency of the AC drive signal.

5. The method of claim 1, further comprising:
after said step of calculating the ratio between the current through the at least one driver to the calculated mechanical equivalent of current through the mechanical components of the handpiece, comparing the calculated ratio to a target ratio; and
setting the frequency of the AC drive signal based on said comparison of the calculated ratio to the target ratio.

6. The method of claim 5, wherein when said step of comparing the calculated ratio to the target ratio comprises comparing the calculated ratio to a target ratio of zero.

7. The method of claim 1, further comprising obtaining the capacitance of the at least one driver from a memory associated with the handpiece.

8. The method of claim 1, wherein; said step of sourcing the AC drive signal comprises:
outputting, from a power supply, either a DC signal or an AC signal at a constant frequency; and
varying, by a signal generator that receives the signal output by the power supply, the frequency of the signal output from the power supply so as to output a variable potential drive signal,
wherein said step of setting the frequency of the AC drive signal comprises regulating the frequency of the signal output by the signal generator.

9. An ultrasonic surgical tool system comprising:
a handpiece having at least one driver that, in response to the application of an AC drive signal, cyclically expands and contracts and a tip, the tip having opposed proximal and distal ends, the proximal end of the tip being coupled to the at least one driver so that the expansions and contractions of the at least one driver cause the proximal end of the tip to vibrate longitudinally, a head at the distal end, the head shaped to when vibrated perform a procedure, and between the proximal and distal ends, a feature that converts the longitudinal vibrations present at the proximal end of the tip to, at the distal end, vibrations that have a longitudinal component and a torsional component;
an assembly for generating a variable AC drive signal that is applied to the at least one driver of the handpiece;
an assembly for measuring a voltage of the AC drive signal that outputs a signal representative of drive signal voltage;
an assembly for measuring a current of the AC drive signal applied to the handpiece that outputs a signal representative of drive signal current; and
a processor that receives the signal representative of drive signal voltage and the signal representative of drive signal current and that is configured to:
determine a target mechanical equivalent of current through mechanical components of the handpiece;
based on the voltage of the AC drive signal, the current of the AC drive signal, a frequency of the AC drive signal and a capacitance of the at least one driver, calculate a mechanical equivalent of current applied to the mechanical components of the handpiece;
compare the target mechanical equivalent of current to the calculated mechanical equivalent of current applied to the mechanical components of the handpiece;
based on the current comparison, set a potential of the AC drive signal output by the assembly that generates the AC drive signal;
based on the voltage of the AC drive signal, the current of the AC drive signal, the frequency of the AC drive signal and the capacitance of the at least one driver, calculate a ratio between current applied to the at least one driver and the mechanical equivalent of current applied to the mechanical components of the handpiece; and
based on the calculated ratio, set the frequency of the AC drive signal output by the assembly that generates the AC drive signal to a frequency between resonant frequencies of two adjacent mechanical resonant modes of the handpiece so a longitudinal component of the vibrations of the tip head of a first one of the mechanical resonant modes at least partially cancels out a longitudinal component of the vibrations of the tip head of a second one of the mechanical resonant modes.

10. The system of claim 9, wherein said processor is further configured to, prior to setting the frequency of the AC drive signal based on the ratio, initially set the frequency of the AC drive signal to a frequency between the resonant frequencies of the two adjacent mechanical resonant modes of the handpiece so the longitudinal component of the vibrations of the tip head of the first one of the mechanical resonant modes at least partially cancels out the longitudinal component of the vibrations of the second one of the mechanical resonant modes.

11. The system of claim 9, wherein the processor is configured to calculate the mechanical equivalent of current applied to the mechanical components of the handpiece by determining the difference between the current of the AC drive signal and the current applied to the at least one driver.

12. The system of claim 11, wherein the processor is configured to determine the current applied to the at least one driver as a function of the capacitance of the at least one driver and the voltage and frequency of the AC drive signal.

13. The system of claim 9, wherein the processor is configured to:
determine if the calculated ratio between the current applied to the at least one driver and the mechanical equivalent of current applied to the mechanical components of the handpiece is substantially equal to a target ratio; and
responsive to determining that the calculated ratio is not substantially equal to the target ratio, adjust the frequency of the AC drive signal based on the calculated ratio.

14. The system of claim 13, wherein the target ratio is zero.

15. The system of claim 9, wherein the processor is further configured to:
obtain from a memory associated with the handpiece data representative of the capacitance of the at least one driver; and
at least upon initial activation of said system:
calculate the mechanical equivalent of current applied to the mechanical components of the handpiece based on the driver capacitance data obtained from the handpiece memory; and
calculate the ratio between current applied to the at least one driver and the mechanical equivalent of current applied to the mechanical components of the handpiece based on the driver capacitance data read from the handpiece memory.

16. The system of claim 9, wherein the processor is further configured to:
receive a signal representative of a user-entered command indicating a desired magnitude of vibrations for the handpiece tip; and based on the signal representative of the user-entered command indicating the desired magnitude of vibrations for the handpiece tip, determine the target mechanical equivalent of current.

17. The system of claim 9, wherein:

the assembly that generates the AC drive signal includes a power supply that outputs a signal at a constant voltage and a variable amplifier that receives the signal output by the power supply and that is configured to amplify the signal from the power supply so as to output a variable potential drive signal; and the processor is connected to said amplifier to set the potential of the drive signal output by said amplifier by regulating the gain of said amplifier.

18. The system of claim 17, wherein the processor is connected to said amplifier to set the potential and frequency of the AC drive signal applied to the at least one driver by regulating the frequency and amplitude of the signal output by said amplifier.

19. The system of claim 9, wherein the feature on the tip is formed with grooves that are shaped so that, as a result of said grooves being present the longitudinal vibrations applied to the tip from said at least one driver are converted into the vibrations having the longitudinal component and the torsional component.

20. The system of claim 19, wherein said grooves are helically shaped so as to curve around a longitudinal axis of the tip.

* * * * *